(12) United States Patent
Nichols et al.

(10) Patent No.: US 12,038,444 B2
(45) Date of Patent: *Jul. 16, 2024

(54) PSEUDO-ELECTROPHEROGRAM CONSTRUCTION FROM PEPTIDE LEVEL MASS SPECTROMETRY DATA

(71) Applicant: Protein Metrics, LLC, Boston, MA (US)

(72) Inventors: Andrew Nichols, Redwood City, CA (US); Marshall Bern, San Carlos, CA (US); Yong Joo Kil, Fremont, CA (US); Eric Carlson, Cupertino, CA (US)

(73) Assignee: Protein Metrics, LLC, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/828,465

(22) Filed: May 31, 2022

(65) Prior Publication Data

US 2022/0291229 A1 Sep. 15, 2022

Related U.S. Application Data

(63) Continuation of application No. 16/859,758, filed on Apr. 27, 2020, now Pat. No. 11,346,844.

(Continued)

(51) Int. Cl.
*G01N 33/68* (2006.01)
*H01J 49/00* (2006.01)

(52) U.S. Cl.
CPC ...... *G01N 33/6848* (2013.01); *H01J 49/0036* (2013.01); *H01J 49/004* (2013.01)

(58) Field of Classification Search
None
See application file for complete search history.

(56) References Cited

U.S. PATENT DOCUMENTS

| 4,464,650 A | 8/1984 | Eastman et al. |
| 4,558,302 A | 12/1985 | Welch |

(Continued)

FOREIGN PATENT DOCUMENTS

| WO | WO2011/127544 A1 | 10/2011 | |
| WO | WO 2015/031820 | * 3/2015 | ........... G01N 27/447 |

OTHER PUBLICATIONS

ZNova Deconvolution retrieved from internet https://web.archive.org/web/20141106214830/http://www.enovatia.com:80/downloads/manuals/promass/Help/html/prom2cdq.htm (Year: 2014).*

(Continued)

*Primary Examiner* — Xiaoyun R Xu
(74) *Attorney, Agent, or Firm* — Shay Glenn LLP

(57) ABSTRACT

Methods and apparatuses for the identification and/or characterization of properties of a macromolecule based on mass spectrometry data. Specifically, described herein are methods and apparatuses for converting peptide-level data into a pseudo-intact mass spectra. Also described herein are methods and apparatuses for converting peptide-level data into a pseudo-electropherogram. The methods may be well suited for analyzing proteins and protein complexes, including estimating properties of post-translational modifications of the proteins and protein complexes. Methods may include generating a theoretical graph or spectrum based on peptide-level mass spectrometry data. In some embodiments, the theoretical graph may be a theoretical intact mass spectrum or a theoretical charge distribution spectrum.

20 Claims, 25 Drawing Sheets

Related U.S. Application Data

(60) Provisional application No. 62/839,507, filed on Apr. 26, 2019.

(56) References Cited

U.S. PATENT DOCUMENTS

| | | |
|---|---|---|
| 4,814,764 A | 3/1989 | Middleton |
| 5,343,554 A | 8/1994 | Koza et al. |
| 5,910,655 A | 6/1999 | Skilling |
| 5,995,989 A | 11/1999 | Gedcke et al. |
| 6,094,627 A | 7/2000 | Peck et al. |
| 6,393,393 B1 | 5/2002 | Kawahara |
| 6,535,555 B1 | 3/2003 | Bordes et al. |
| 6,798,360 B1 | 9/2004 | Qian et al. |
| 6,906,320 B2 | 6/2005 | Sachs et al. |
| 7,006,567 B2 | 2/2006 | Frossard et al. |
| 7,283,684 B1 | 10/2007 | Keenan |
| 7,283,937 B2 | 10/2007 | Goldberg |
| 7,297,940 B2 | 11/2007 | Bern |
| 7,397,961 B2 | 7/2008 | Keeney et al. |
| 7,400,772 B1 | 7/2008 | Keenan |
| 7,402,438 B2 | 7/2008 | Goldberg |
| 7,429,727 B2 | 9/2008 | Bern |
| 7,496,453 B2 | 2/2009 | Chau |
| 7,680,670 B2 | 3/2010 | Lamblin et al. |
| 7,979,258 B2 | 7/2011 | Goldberg et al. |
| 8,004,432 B2 | 8/2011 | Kawato |
| 8,023,750 B2 | 9/2011 | Raveendran et al. |
| 8,077,988 B2 | 12/2011 | Donoho |
| 8,108,153 B2 | 1/2012 | Bern |
| 8,428,889 B2 | 4/2013 | Wright |
| 8,511,140 B2 | 8/2013 | Gorenstein et al. |
| 8,598,516 B2 | 12/2013 | Sapargaliyev et al. |
| 8,645,145 B2 | 2/2014 | Subbaraman et al. |
| 9,385,751 B2 | 7/2016 | Kletter |
| 9,571,122 B2 | 2/2017 | Kletter |
| 9,640,376 B1 | 5/2017 | Becker et al. |
| 9,859,917 B2 | 1/2018 | Kletter |
| 10,199,206 B2 | 2/2019 | Becker et al. |
| 10,354,421 B2 | 7/2019 | Becker et al. |
| 10,510,521 B2 | 12/2019 | Kil et al. |
| 10,546,736 B2 | 1/2020 | Bern et al. |
| 10,665,439 B2 | 5/2020 | Bern |
| 10,879,057 B2 | 12/2020 | Kil et al. |
| 10,991,558 B2 | 4/2021 | Bern et al. |
| 11,127,575 B2 | 9/2021 | Bern |
| 11,276,204 B1 | 3/2022 | Kletter |
| 11,289,317 B2 | 3/2022 | Kil et al. |
| 11,346,844 B2 | 5/2022 | Nichols et al. |
| 2002/0068366 A1 | 6/2002 | LaDine et al. |
| 2003/0031369 A1 | 2/2003 | Le Pennec et al. |
| 2003/0200032 A1 | 10/2003 | Keating et al. |
| 2003/0218634 A1 | 11/2003 | Kuchinsky et al. |
| 2004/0102906 A1 | 5/2004 | Roder |
| 2004/0160353 A1 | 8/2004 | Cirillo et al. |
| 2005/0047670 A1 | 3/2005 | Qian et al. |
| 2005/0063864 A1 | 3/2005 | Sano et al. |
| 2005/0276326 A1 | 12/2005 | Drezner |
| 2008/0010309 A1 | 1/2008 | Sugita |
| 2008/0025394 A1 | 1/2008 | Francois et al. |
| 2008/0260269 A1 | 10/2008 | Thiagarajan |
| 2009/0012931 A1 | 1/2009 | Appa et al. |
| 2009/0052528 A1 | 2/2009 | Jeon et al. |
| 2009/0179147 A1 | 7/2009 | Milgram et al. |
| 2010/0124785 A1 | 5/2010 | Bern |
| 2010/0288917 A1 | 11/2010 | Satulovsky et al. |
| 2010/0288918 A1 | 11/2010 | Satulovsky |
| 2011/0093205 A1 | 4/2011 | Bern |
| 2012/0047098 A1 | 2/2012 | Reem |
| 2012/0245857 A1 | 9/2012 | Lee et al. |
| 2013/0080073 A1 | 3/2013 | de Corral |
| 2013/0144540 A1 | 6/2013 | Bern et al. |
| 2013/0226594 A1 | 8/2013 | Fuchs et al. |
| 2013/0262809 A1 | 10/2013 | Wegener |
| 2013/0275399 A1 | 10/2013 | Amit et al. |
| 2013/0289892 A1 | 10/2013 | Satoh |
| 2014/0045273 A1 | 2/2014 | Cerda et al. |
| 2014/0164444 A1 | 6/2014 | Bowen et al. |
| 2015/0319268 A1 | 11/2015 | Callard et al. |
| 2015/0369782 A1 | 12/2015 | Kageyama |
| 2016/0077926 A1 | 3/2016 | Mutalik et al. |
| 2016/0180555 A1 | 6/2016 | Matsuo |
| 2016/0215028 A1 | 7/2016 | Mutharia et al. |
| 2016/0268112 A1 | 9/2016 | Yip et al. |
| 2018/0301326 A1 | 10/2018 | Bern et al. |
| 2020/0075300 A1 | 3/2020 | Bern |
| 2020/0413066 A1 | 12/2020 | Lavaud |
| 2021/0335589 A1 | 10/2021 | Bern et al. |
| 2022/0076936 A1 | 3/2022 | Bern |
| 2022/0207778 A1 | 6/2022 | Kletter |
| 2023/0268168 A1 | 8/2023 | Bern et al. |
| 2023/0343569 A1 | 10/2023 | Bern et al. |

OTHER PUBLICATIONS

Jeong et al.; Flashdeconv:ultrafast, high-quality feature deconvolution for top-down proteomics; Cell Systems; 10(2); pp. 213-218; doi.org/10,1016/j.cels.2020.01.003; 13 pages; Feb. 2020.

Marty et al.; Bayesian deconvolution of mass and ion mobility spectra: from binary interactions to polydisperse ensembles; Analytical Chemistry: 87(8): pp. 4370-4376; 7 pages; (Author Manuscript): Apr. 2015.

Marty; What can unidec do for you? Mar. 24, 2015| 28 pages; retrieved from the internet (http://unidec.chem.ox.ac.uk/UniDecTutorial.pdf) on Oct. 25, 2022.

Klammer et al.; Peptide charge state determination for low-resolution tandem mass spectra; In2005 IEEE Computational Systems Bioinformatics Conference (CSB'05); pp. 175-185; Aug. 8, 2005.

Krokhin et al.; An improved model for prediction of retention times of tryptics peptides in ion pair reversed-phase HPLC: its application to protein peptide mapping by off-line HPLC-MALDI MS; Molecular and Cellular Proteomics; 3(9); pp. 908-919; Sep. 2004.

Lu et al.; Improved peak detection and deconvolution of native electrospray mass spectra from large protein complexes; Journal of the American Society for Mass Spectrometry; 26(12); pp. 2141-2151; Dec. 2015.

Schreiber et al.; Using PeakView(TM) software with the XIC manager for screening and identification with high confidence based on high resolution and accurate mass LC-MS/MS; AB Sciex; Food & Environmental; (Pub. # 2170811-03); 5 pgs.; Apr. 2, 2011.

Shi et al.; Feature-based image set compression; 2013 IEEE International Conference on Multimedia and Expo (ICME); IEEE; pp. 1-6; Jul. 15, 2013.

Shi et al.; Multi-model prediction for image set compression; 2013 Visual Communications and Image Processing (VCIP); IEEE; pp. 1-6; Nov. 17, 2013.

Thermo Fisher Scientific, Inc.; Thermo Xcaliber: Qualitative Analysis (User Guide); Revision B; 290 pgs.; Sep. 2010.

Valot et al.; MassChroQ: A versatile tool for mass spectrometry quantification; Proteomics; 11(17); 23 pgs.; Sep. 2011.

VanBramer; An Introduction to Mass Spectrometry; Wider University; 38 pgs.; © 1997; (revised) Sep. 2, 1998.

Waters Corporation; Biopharmalynx: A new bioinformatics tool for automated LC/MS peptide mapping assignment; 6 pages retrived May 17, 2018 from the internet (http://www.waters.com/webassets/cms/library/docs/720002754en.pdf); Sep. 2008.

Waters Corporation; MassLynx 4.1 Getting started guide; 71500113203/RevisionA; 96 pages; retrieved May 17, 2018 from the internet (http://turroserver.chem.columbia.edu/group/instrument/HPLC/HPLC%20Getting%20Started.pdf) ; 2005.

Waters Corporation; QuanLynx User's Guide; Version 4.0; 125 pages; retrived May 17, 2018 from the internet ( http://www.waters.com/webassets/cms/support/docs/quanlynx_40.pdf); Feb. 15, 2002.

Wehofsky et al.; Isotopic deconvolution of matrix-assisted laser desorption/ionization mass spectra for substance-class specific analysis of complex samples; European Journal of Mass Spectrometry; 7(1); pp. 39-46; Feb. 1, 2001.

(56) References Cited

OTHER PUBLICATIONS

Xu et al.; Deconvolution in mass spectrometry based proteomics; Rapid Communications in Mass Spectrometry; 32(10); pp. 763-774; May 30, 2018.

Yang et al.; Detecting low level sequence variants in recombinant monoclonal antibodies; mAbs 2 (3); pp. 285-298; May/Jun. 2010.

Yang et al.; Hybrid mass spectrometry approaches in glycoprotein analysis and their usage in scoring biosimilarity; Nature Communications; 7(1); pp. 1-10; Nov. 8, 2016.

Ziv et al.; A universal algorithm for sequential data compression; IEEE Trans. on Information Theory; IT-23(3); pp. 337-343; May 1977.

Ziv et al.; Compression of individual sequences via variable-rate coding; IEEE Trans. on Information Theory; IT-24(5); pp. 530-536; Sep. 1978.

Kil et al.; U.S. Appl. No. 17/706,539 entitled "Interactive analysis of mass spectrometry data," filed Mar. 28, 2022.

Khelifati et al.; Corad: Correlation-aware compression of massive time series using sparse dictionary coding. In2019 IEEE International Conference on Big Data (Big Data); IEEE; pp. 2289-2298; Dec. 9, 2019.

Kletter et al.; U.S. Appl. No. 18/460,028 entitled "Data Compression for multidimensional time series data," filed Sep. 1, 2023.

\* cited by examiner

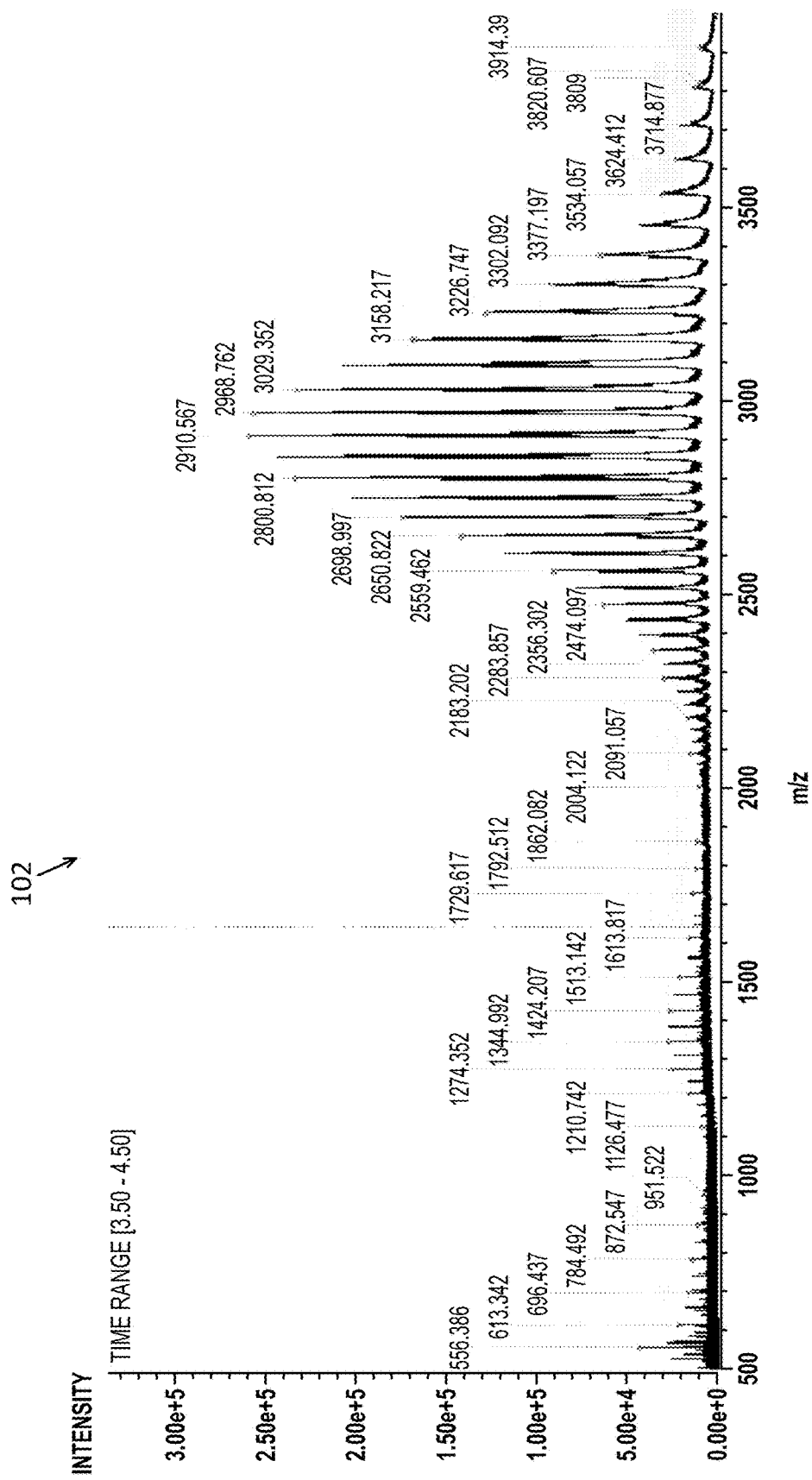
FIG. 1A(1)

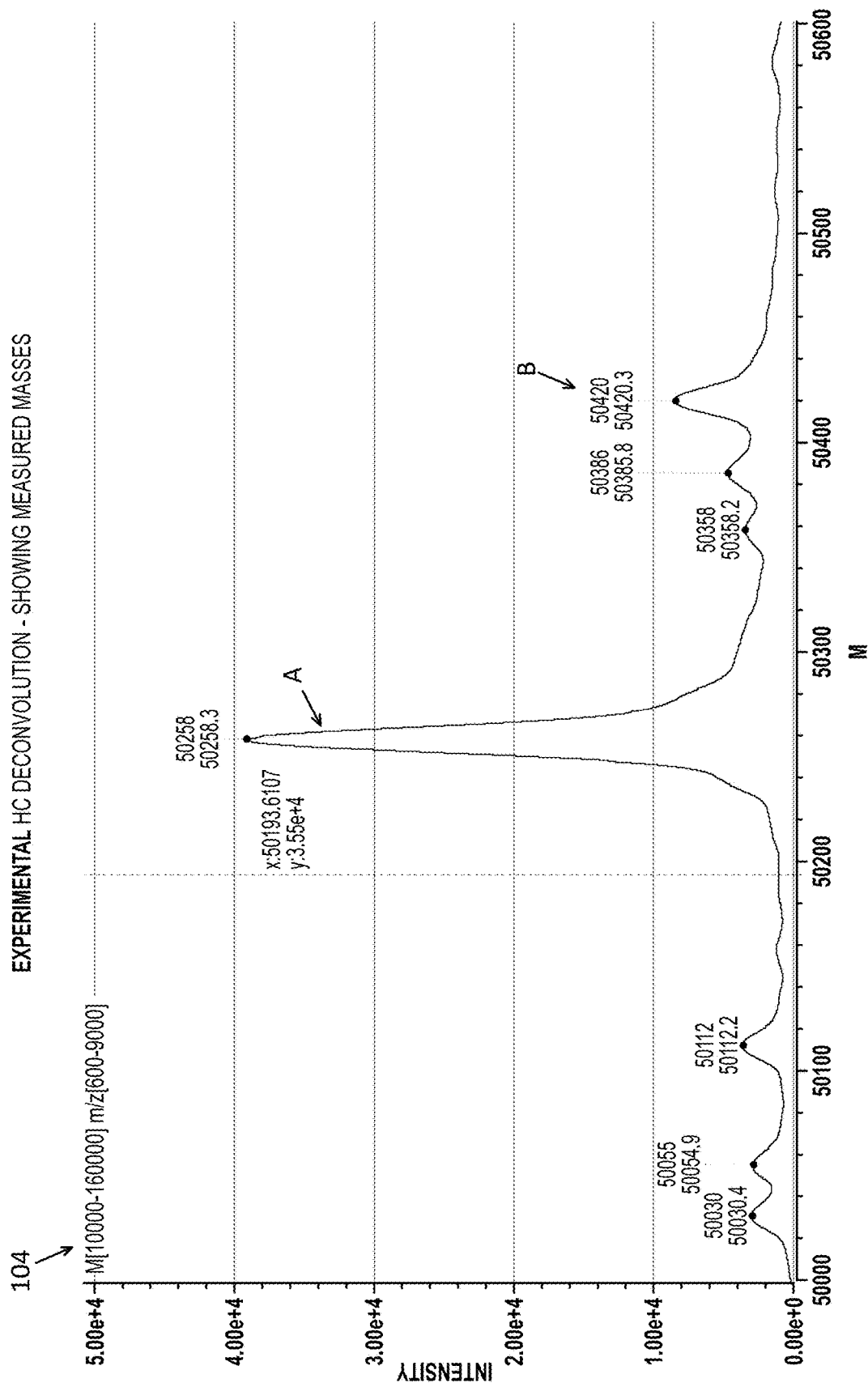
FIG. 1A(2)

108

MODIFICATION QUANTIFICATION AT PEPTIDE LEVEL

| Digest Name | Tryptic |
|---|---|
| MS Id | 1 |
| [runAliasName] | |

| Protein name ↑ | Sequence (unformatted) ↑ | Var. Pos. Protein ↑ | Mod. Summary ↑ | Mod. Names ↑ | Archway-Control-Native-Tryp_RP11-Try |
|---|---|---|---|---|---|
| C40B110_HC | DNSENALYLQMNSLR | 77 | N5(Deamidated/0.9840) | Deamidated/0.9840 | 0.752 |
| | | 84 | N12(Deamidated/0.9840) | Deamidated/0.9840 | 1.79 |
| | DTLMISR | 251 | D1(Asp-Succinimide/-18.0106) | Asp-Succinimide/-18.0106 | 18.3 |
| | | 254 | M4(Oxidation/-15.9949) | Oxidation/-15.9949 | 29.1 |
| | DYFPEPVTVSWNSGALTSGVHTFPAVLQSSGLYSLSSVVTVPSSSLGTQTYICNVNHKPSNTK | 160 | W11(Trp-2/-2.0151) | Trp-2/-2.0151 | 1.82 |
| | | 177 | Q28(Deamidated/0.9840) | Deamidated/0.9840 | 1.8 |
| | | 198 | Q49(Asn-Succinimide/-17.0265) | Asn-Succinimide/-17.0265 | 0.118 |
| | | 198 | Q49(Deamidated/0.9840) | Deamidated/0.9840 | 0.917 |
| | | 205 | N56(Deamidated/0.9840) | Deamidated/0.9840 | 0.917 |
| | EEQYNSTYR | 299 | N5(NG1yean/-1054.3700) | NG1yean/-1054.3700 | 0.666 |
| | | | N5(NG1yean/-1216.4229) | NG1yean/-1216.4229 | 4.19 |
| | | | N5(NG1yean/-1241.4545) | NG1yean/-1241.4545 | 4.1 |
| | | | N5(NG1yean/-1298.4760) | NG1yean/-1298.4760 | 5.89 |
| | | | N5(NG1yean/-1444.5339) | NG1yean/-1444.5339 | 74.5 |
| | | | N5(NG1yean/-1606.5867) | NG1yean/-1606.5867 | 9.88 |
| | | | N5(NG1yean/-1768.6395) | NG1yean/-1768.6395 | 0.412 |
| | EVQLLESGGGLVQPGGSLR | 1 | E1(G1u-pyro-G1u/-18.0106) | G1u-pyro-G1u/-18.0106 | 1.92 |
| | FNWYVDGVEVHNAK | 278 | N2(Deamidated/0.9840) | Deamidated/0.9840 | 1.35 |
| | | 282 | D6(Asp-Succinimide/-18.0106) | Asp-Succinimide/-18.0106 | 0.127 |
| | | 288 | N12(Deamidated/0.9840) | Deamidated/0.9840 | 2.39 |
| | GFYPSDIAVEWESNGQPENNYK | 386 | N14(Deamidated/0.9840) | Deamidated/0.9840 | 25.7 |
| | | 391 | N19(Deamidated/0.9840) | Deamidated/0.9840 | 6.07 |
| | GGSGMDLWGQGTLVTVSSASTK | 104 | S3(oxidationSQ/15.9949) | oxidationSQ/15.9949 | 0.144 |
| | | 106 | M5(Oxidation/15.9949) | Oxidation/15.9949 | 0.664 |
| | | 111 | Q10(Deamidated/0.9840) | Deamidated/0.9840 | 1.48 |
| | NQVSLTCLVK | 363 | N1(Deamidated/0.9840) | Deamidated/0.9840 | 1.17 |
| | | 364 | Q2(Deamidated/0.9840) | Deamidated/0.9840 | 1.75 |
| | TPEVTCVVVDVSHEDPEVK | 263 | C6(Oxidation/15.9949) | Oxidation/15.9949 | 0.0311 |
| | | 269 | S12(oxidationSQ/15.9949) | oxidationSQ/15.9949 | 0.0749 |
| | | 270 | H13(Oxidation/15.9949) | Oxidation/15.9949 | 0.0749 |
| | VVSVLTVLHQDWLNGK | 313 | Q10(Asn-Succinimide/-17.0265) | Asn-Succinimide/-17.0265 | 2.3 |
| | | 317 | N14(Deamidated/0.9840) | Deamidated/0.9840 | 21.9 |
| | WQQGNVFSCSVMHEALHNHYTQK | 421 | Q3(Deamidated/0.9840) | Deamidated/0.9840 | 0.129 |
| | | 423 | N5(Deamidated/0.9840) | Deamidated/0.9840 | 0.486 |
| | | 430 | M12(Oxidation/15.9949) | Oxidation/15.9949 | 2.53 |
| | | 435 | H17(Oxidation/15.9949) | Oxidation/15.9949 | 0.135 |
| | | 436 | N18(Deamidated/0.9840) | Deamidated/0.9840 | 1.82 |
| | | 437 | H19(Oxidation/15.9949) | Oxidation/15.9949 | 0.135 |
| | | 440 | Q22(Asn-Succinimide/-17.0265) | Asn-Succinimide/-17.0265 | 0.162 |

FIG. 1B(1)

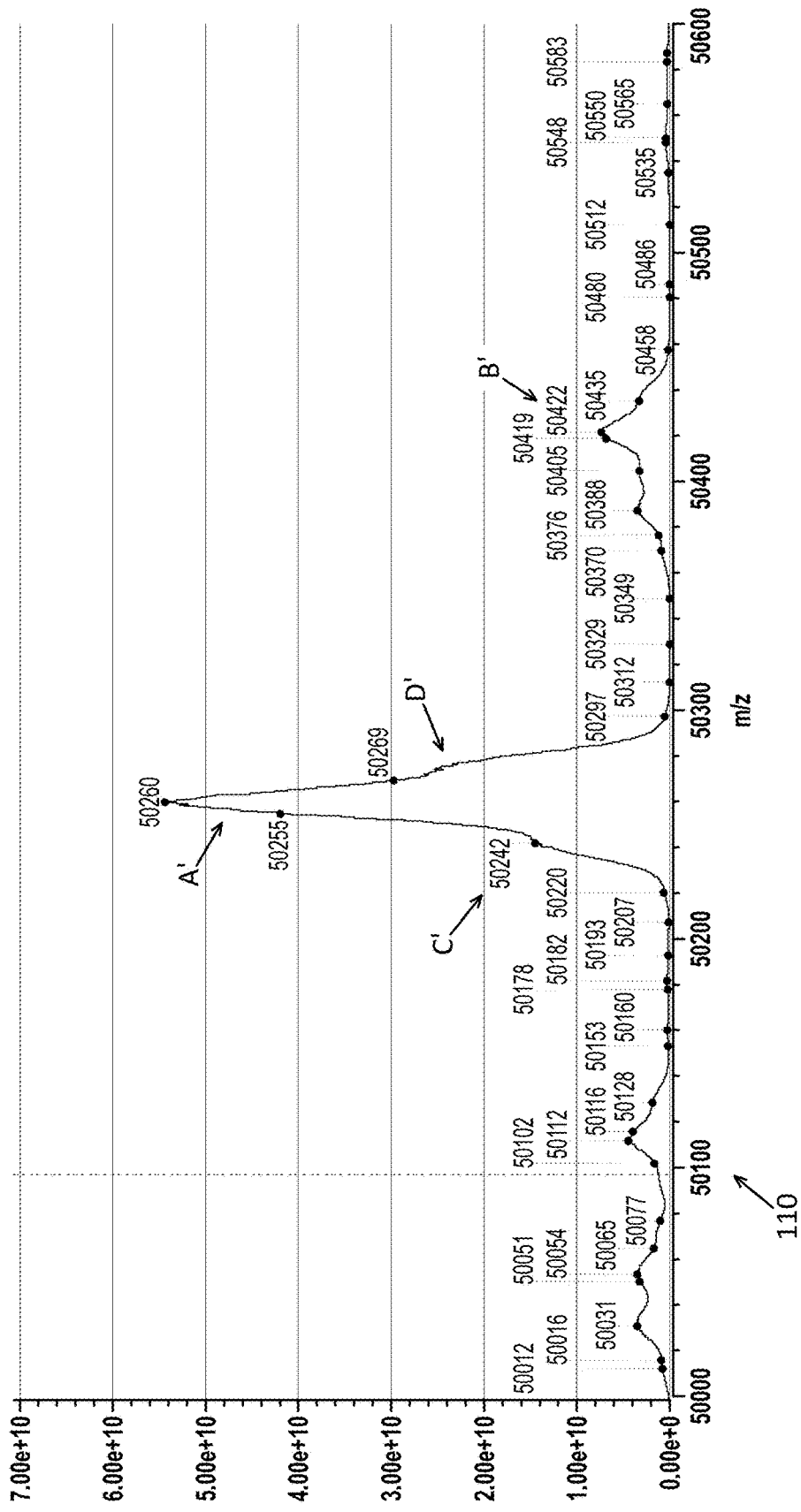
FIG. 1B(2)

108

MODIFICATION QUANTIFICATION AT PEPTIDE LEVEL

| Digest Name | Tryptic |
|---|---|
| MS Id | 1 |
| [runAliasName] | |

| Protein name ↑ | Sequence (unformatted) ↑ | Var. Pos. Protein ↑ | Mod. Summary ↑ | Mod. Names ↑ | Archway-Control-Native-Tryp_RP11-Try |
|---|---|---|---|---|---|
| C40B110_HC | DNSENALYLQMNSLR | 77 | N5(Deamidated/0.9840) | Deamidated/0.9840 | 0.752 |
| | | 84 | N12(Deamidated/0.9840) | Deamidated/0.9840 | 1.79 |
| | DTLMISR | 251 | D1(Asp-Succinimide/-18.0106) | Asp-Succinimide/-18.0106 | 18.3 |
| | | 254 | M4(Oxidation/-15.9949) | Oxidation/-15.9949 | 29.1 |
| | DYFPEPVTVSWNSGALTSGVHTFPAVLQSSGLYSLSSVVTVPSSSLGTQTYICNVNHKPSNTK | 160 | W11(Trp-2/-2.0151) | Trp-2/-2.0151 | 1.82 |
| | | 177 | Q28(Deamidated/0.9840) | Deamidated/0.9840 | 1.8 |
| | | 198 | Q49(Asn-Succinimide/-17.0265) | Asn-Succinimide/-17.0265 | 0.118 |
| | | | Q49(Deamidated/0.9840) | Deamidated/0.9840 | 0.917 |
| | | 205 | N56(Deamidated/0.9840) | Deamidated/0.9840 | 0.917 |
| | EEQYNSTYR | 299 | N5(NG1yean/-1054.3700) | NG1yean/-1054.3700 | 0.666 |
| | | | N5(NG1yean/-1216.4229) | NG1yean/-1216.4229 | 4.19 |
| | | | N5(NG1yean/-1241.4545) | NG1yean/-1241.4545 | 4.1 |
| | | | N5(NG1yean/-1298.4760) | NG1yean/-1298.4760 | 5.89 |
| | | | N5(NG1yean/-1444.5339) | NG1yean/-1444.5339 | 74.5 |
| | | | N5(NG1yean/-1606.5867) | NG1yean/-1606.5867 | 9.88 |
| | | | N5(NG1yean/-1768.6395) | NG1yean/-1768.6395 | 0.412 |
| | EVQLLESGGGLVQPGGSLR | 1 | E1(G1u-pyro-G1u/-18.0106) | G1u-pyro-G1u/-18.0106 | 1.92 |
| | FNWYVDGVEVHNAK | 278 | N2(Deamidated/0.9840) | Deamidated/0.9840 | 1.35 |
| | | 282 | D6(Asp-Succinimide/-18.0106) | Asp-Succinimide/-18.0106 | 0.127 |
| | | 288 | N12(Deamidated/0.9840) | Deamidated/0.9840 | 2.39 |
| | GFYPSDIAVEWESNGQPENNYK | 386 | N14(Deamidated/0.9840) | Deamidated/0.9840 | 25.7 |
| | | 391 | N19(Deamidated/0.9840) | Deamidated/0.9840 | 6.07 |
| | GGSGMDLWGQGTLVTVSSASTK | 104 | S3(oxidationSQ/15.9949) | oxidationSQ/15.9949 | 0.144 |
| | | 106 | M5(Oxidation/15.9949) | Oxidation/15.9949 | 0.664 |
| | | 111 | Q10(Deamidated/0.9840) | Deamidated/0.9840 | 1.48 |
| | NQVSLTCLVK | 363 | N1(Deamidated/0.9840) | Deamidated/0.9840 | 1.17 |
| | | 364 | Q2(Deamidated/0.9840) | Deamidated/0.9840 | 1.75 |
| | TPEVTCVVVDVSHEDPEVK | 263 | C6(Oxidation/15.9949) | Oxidation/15.9949 | 0.0311 |
| | | 269 | S12(oxidationSQ/15.9949) | oxidationSQ/15.9949 | 0.0749 |
| | | 270 | H13(Oxidation/15.9949) | Oxidation/15.9949 | 0.0749 |
| | VVSVLTVLHQDWLNGK | 313 | Q10(Asn-Succinimide/-17.0265) | Asn-Succinimide/-17.0265 | 2.3 |
| | | 317 | N14(Deamidated/0.9840) | Deamidated/0.9840 | 21.9 |
| | WQQGNVFSCSVMHEALHNHYTQK | 421 | Q3(Deamidated/0.9840) | Deamidated/0.9840 | 0.129 |
| | | 423 | N5(Deamidated/0.9840) | Deamidated/0.9840 | 0.486 |
| | | 430 | M12(Oxidation/15.9949) | Oxidation/15.9949 | 2.53 |
| | | 435 | H17(Oxidation/15.9949) | Oxidation/15.9949 | 0.135 |
| | | 436 | N18(Deamidated/0.9840) | Deamidated/0.9840 | 1.82 |
| | | 437 | H19(Oxidation/15.9949) | Oxidation/15.9949 | 0.135 |
| | | 440 | Q22(Asn-Succinimide/-17.0265) | Asn-Succinimide/-17.0265 | 0.162 |

| PROTEIN | POSITION | MOD | LONELY SAMPLE |
|---|---|---|---|
| LC | 31 | S7(Dehydrated/-18.0106) | 1.14 |
| LC | 4 | M4(Oxidation/15.9949) | 1.2 |
| LC | 199 | Q11(Deamidated/0.9840) | 0.139 |
| HC | 253 | M4(Dethiomethyl/-48.0034) | 2.67 |
| HC | 253 | M4(Oxidation/15.9949) | 4.29 |
| HC | 190 | P42(Proline Oxidation/15.9949) | 0.689 |
| HC | 191 | S43(oxidationSQ/15.9949) | 0.751 |
| HC | 352 | L7(Carbonyl/13.9793) | 0.0117 |
| HC | 354 | P9(Oxidation/15.9949) | 1.74 |
| HC | 356 | R11(Oxidation/15.9949) | 0.0148 |
| HC | 359 | M14(Oxidation/15.9949) | 0.667 |
| HC | 277 | N2(Deamidated/0.9840) | 0.0271 |
| HC | 278 | W3(Dioxidation/31.9898) | 0.0655 |
| HC | 387 | Q16(Asn-Succinimide/-17.0265) | 1.63 |
| HC | 131 | P9(Oxidation/15.9949) | 0.195 |
| HC | 363 | Q2(Deamidated/0.9840) | 0.33 |
| HC | 39 | Q1(Gln-pyro-Glu/-17.0265) | 1.82 |
| HC | 39 | Q1(oxidationSQ/15.9949) | 0.321 |
| HC | 43 | Q5(Asn-Succinimide/-17.0265) | 1.09 |
| HC | 47 | W9(Oxidation/15.9949) | 0.321 |
| HC | 48 | M10(Oxidation/15.9949) | 0.473 |
| HC | 402 | D9(Asp-Succinimide/-18.0106) | 0.0372 |
| HC | 312 | Q10(Asn-Succinimide/-17.0265) | 1.97 |
| HC | 314 | W12(Trp-Kynurenin/-3.9949) | 0.0433 |
| HC | 316 | N14(Deamidated/0.9840) | 0.00143 |
| HC | 312 | Q10(Asn-Succinimide/-17.0265) | 1.24 |
| HC | 316 | N14(Deamidated/0.9840) | 4.9 |
| HC | 429 | M12(Oxidation/15.9949) | 2.49 |
| HC | 110 | Q10(Deamidated/0.9840) | 0.265 |
| HC | 298 | NGlycan/1216.4229 | 1.33 |
| HC | 298 | NGlycan/1444.5339 | 29.06 |
| HC | 298 | NGlycan/1606.5867 | 38.43 |
| HC | 298 | NGlycan/1768.6395 | 28.23 |
| HC | 500 | Lysine/128 | 13.97 |

FIG. 2A(1)

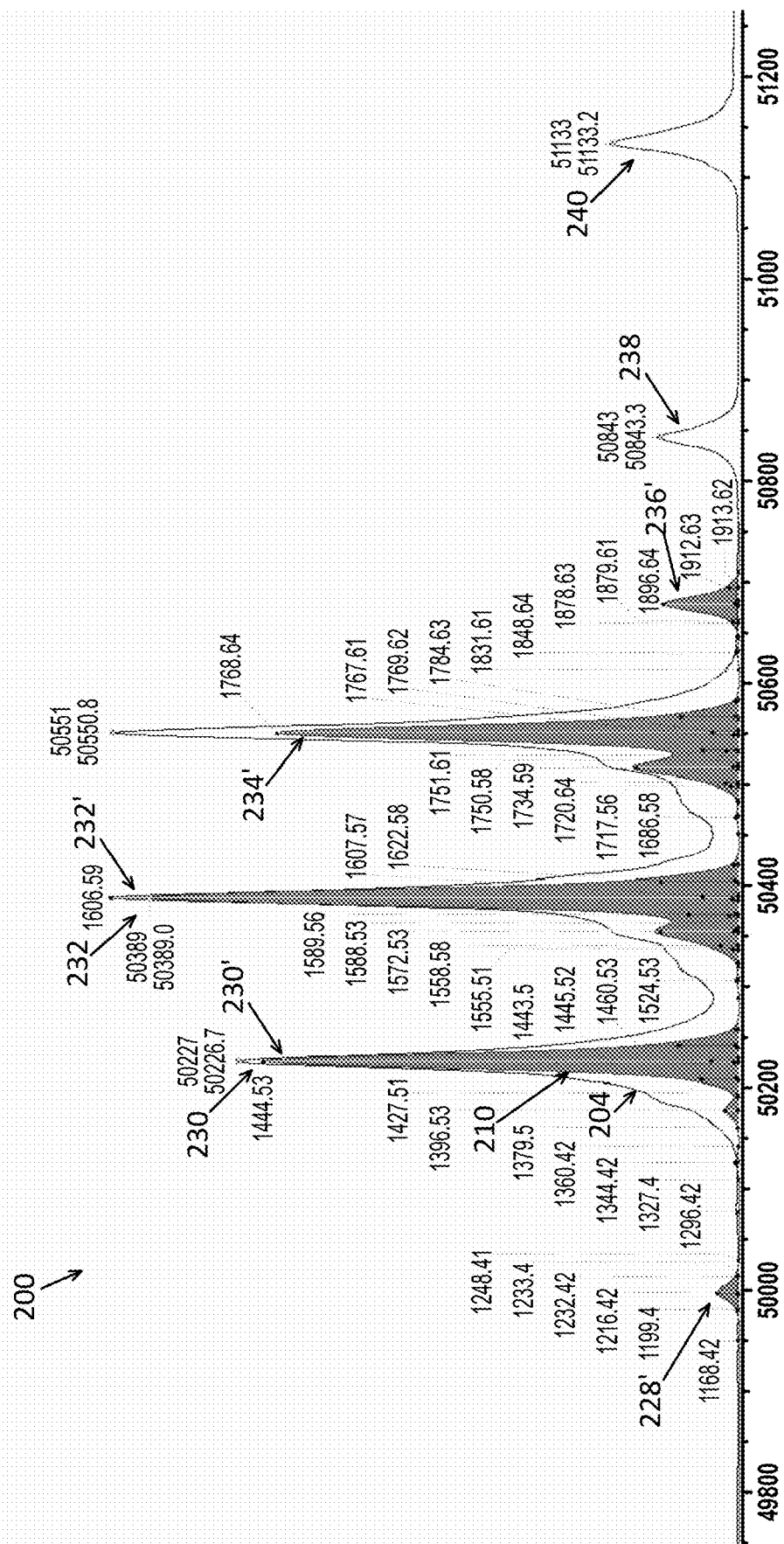
FIG. 2A(2)

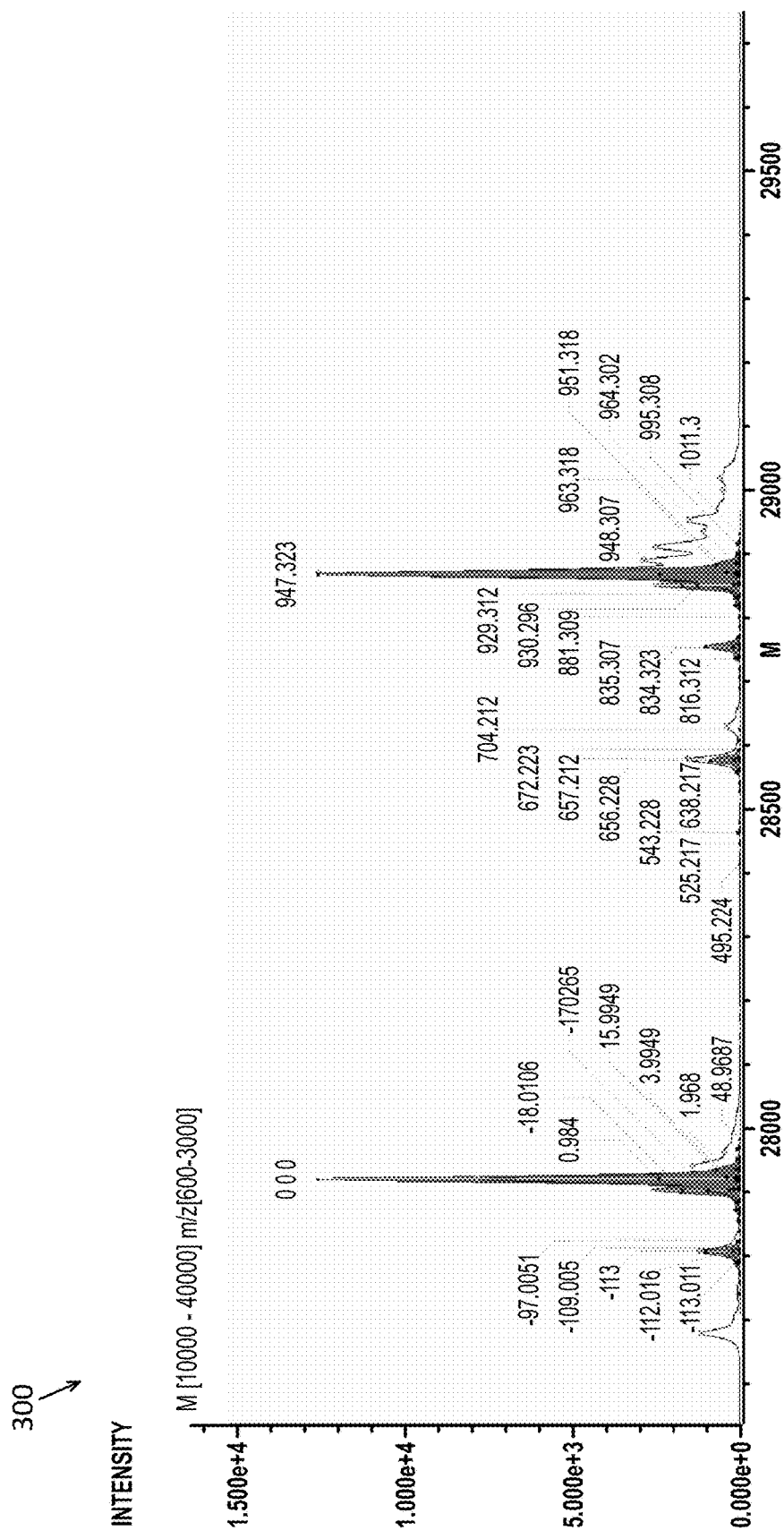
FIG. 3A(1)

| Protein | Position | Mod | Trime |
|---|---|---|---|
| HAGW6_HC | 239 | OGlycan / 947.3230 | 48.27 |
| HAGW6_HC | 29 | OGlycan / 1095.3966 | 35.11 |
| HAGW6_HC | 213 | N1(Deamidated / 0.9840) | 9.9 |
| HAGW6_HC | 500 | CTermIsoLeuceineLoss / -113 | 7.54 |
| HAGW6_HC | 48 | T3(Dehydrated / -18.0106) | 4.93 |
| HAGW6_HC | 194 | N4(Deamidated / 0.9840) | 4.77 |
| HAGW6_HC | 184 | Q2(Asn-Succinimide / -17.0265) | 4.54 |
| HAGW6_HC | 141 | D4(Asp-Succinimide / -18.0106) | 4.01 |
| HAGW6_HC | 151 | W2(Trp-Kynurenin / 3.9949) | 2.98 |
| HAGW6_HC | 239 | OGlycan / 656.2276 | 2.87 |
| HAGW6_HC | 138 | Q1(Gln-pyro-Glu / -17.0265) | 1.73 |
| HAGW6_HC | 119 | N2(Deamidated / 0.9840) | 1.55 |
| HAGW6_HC | 76 | M20(Oxidation / 15.9949) | 1.39 |
| HAGW6_HC | 233 | D4(Asp-Succinimide / -18.0106) | 1.21 |
| HAGW6_HC | 208 | M6(Dethiomethyl / -48.0034) | 1.05 |
| HAGW6_HC | 191 | E1(Glu-pyro-Glu / -18.0106) | 0.988 |
| HAGW6_HC | 244 | Q3(Asn-Succinimide / -17.0265) | 0.936 |
| HAGW6_HC | 120 | T3(Dehydrated / -18.0106) | 0.74 |
| HAGW6_HC | 151 | W2(Oxidation / 15.9949) | 0.739 |
| HAGW6_HC | 208 | M6(Oxidation / 15.9949) | 0.595 |
| HAGW6_HC | 172 | M7(Dehydrated / -18.0106) | 0.575 |
| HAGW6_HC | 239 | S3(OGlycan / 656.2276) | 0.507 |
| HAGW6_HC | 130 | N8(Deamidated / 0.9840) | 0.507 |
| HAGW6_HC | 163 | N14(Deamidated / 0.9840) | 0.478 |
| HAGW6_HC | 178 | Y3(Oxidation / 15.9949) | 0.468 |
| HAGW6_HC | 230 | E1(Glu-pyro-Glu / -18.0106) | 0.444 |
| HAGW6_HC | 73 | W17(Trioxidation / 47.9847) | 0.436 |
| HAGW6_HC | 78 | D22(Oxidation / 15.9949) | 0.29 |
| HAGW6_HC | 80 | W24(Trioxidation / 47.9847) | 0.279 |
| HAGW6_HC | 205 | N3(Deamidated / 0.9840) | 0.262 |
| HAGW6_HC | 102 | N4(Deamidated / 0.9840) | 0.254 |
| HAGW6_HC | 221 | Y1(Oxidation / 15.9949) | 0.234 |
| HAGW6_HC | 80 | W24(Oxidation / 15.9949) | 0.224 |
| HAGW6_HC | 85 | H29(Oxidation / 15.9949) | 0.224 |
| HAGW6_HC | 129 | Y7(Oxidation / 15.9949) | 0.209 |
| HAGW6_HC | 169 | Y4(Oxidation / 15.9949) | 0.209 |
| HAGW6_HC | 78 | D22(Dehydrated / -18.0106) | 0.207 |
| HAGW6_HC | 152 | C3(Oxidation / 15.9949) | 0.202 |
| HAGW6_HC | 153 | Y4(Oxidation / 15.9949) | 0.202 |
| HAGW6_HC | 154 | N5(Oxidation / 15.9949) | 0.202 |
| HAGW6_HC | 151 | W2(Dioxidation / 31.9898) | 0.189 |
| HAGW6_HC | 85 | H29(Dioxidation / 31.9898) | 0.184 |
| HAGW6_HC | 38 | Y1(Oxidation / 15.9949) | 0.173 |
| HAGW6_HC | 176 | N1(Deamidated / 0.9840) | 0.166 |
| HAGW6_HC | 73 | W17(Dioxidation / 31.9898) | 0.16 |
| HAGW6_HC | 200 | Y10(Oxidation / 15.9949) | 0.137 |
| HAGW6_HC | 80 | W24(Dioxidation / 31.9898) | 0.11 |
| HAGW6_HC | 84 | H28(Dioxidation / 31.9898) | 0.11 |
| HAGW6_HC | 101 | Q3(Asn-Succinimide / -17.0265) | 0.101 |
| HAGW6_HC | 80 | W24(Trp-2 / -2.0151) | 0.0633 |
| HAGW6_HC | 164 | Q15(Asn-Succinimide / -17.0265) | 0.0151 |
| HAGW6_HC | 149 | NTerm(Formyl / 27.9949) | 0.00688 |

FIG. 3A(2)

| Delta Mass | Proteins | Chains | Positions | Mod Values | Contribution Delta Mass | Contribution Protein |
|---|---|---|---|---|---|---|
| -129.042 | 0;0 | 0;0 | 184;213;500 | -17.0265;0.984;-113 | 0.503332 | 0.08011498 |
| -127.016 | 0;0 | 0;0 | 141;151;500 | -18.0106;3.9949;-113 | 0.446165 | 2.85E-05 |
| -127.016 | 0;0 | 0;0 | 48;151;500 | -18.0106;3.9949;-113 | 0.553835 | 3.54E-05 |
| -126.032 | 0;0 | 0;0 | 138;151;500 | -17.0265;3.9949;-113 | 0.270159 | 1.20E-05 |
| -126.032 | 0;0 | 0;0 | 153;184;500 | 3.9949;-17.0265;-113 | 0.729841 | 3.25E-05 |
| -115.016 | 0;0 | 0;0 | 76;141;500 | 15.9949;18.0106;-113 | 0.446165 | 1.50E-05 |
| -115.016 | 0;0 | 0;0 | 48;76;500 | -18.0106;15.9949;-113 | 0.553835 | 1.61E-05 |
| -115.035 | 0;0 | 0;0 | 80;500 | -2.0153;-113 | 1 | 1.40E-05 |
| -114.032 | 0;0 | 0;0 | 76;184;500 | 15.9949;-17.0265;-113 | 1 | 1.48E-05 |
| -113 | 0 | 0 | 500 | -113 | 1 | 0.02280528 |

FIG. 3B

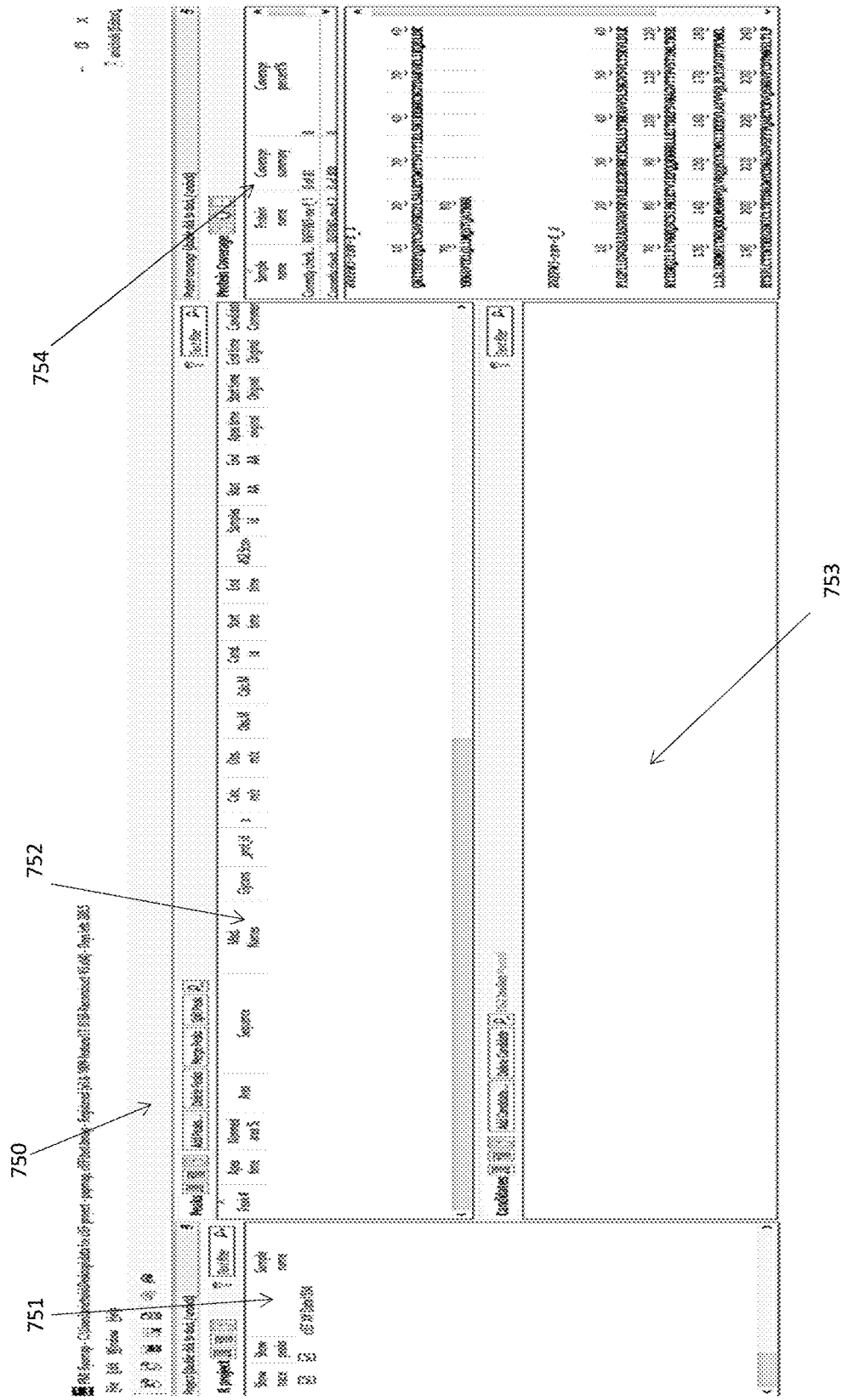
FIG. 7A(1)

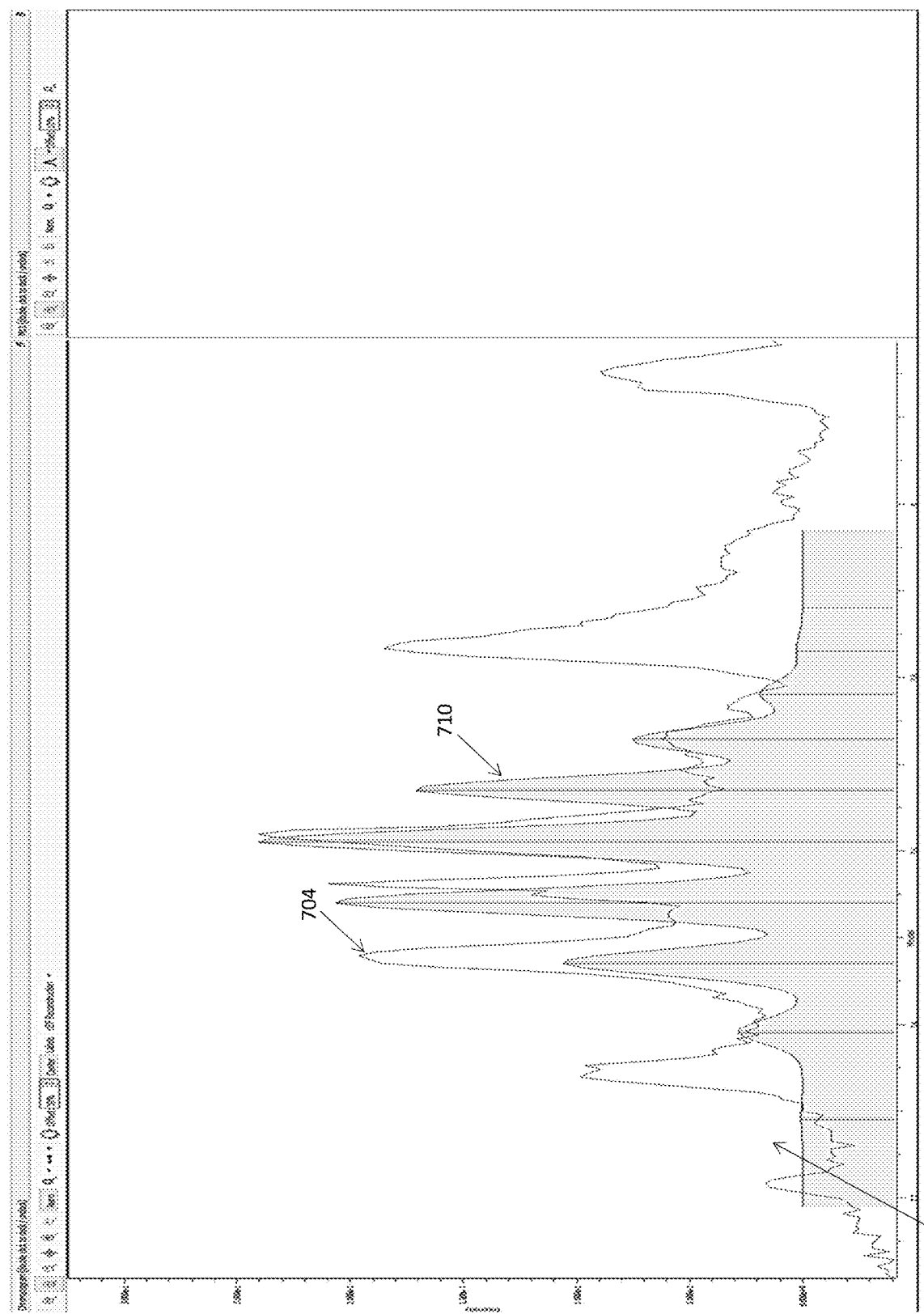
FIG. 7A(2)

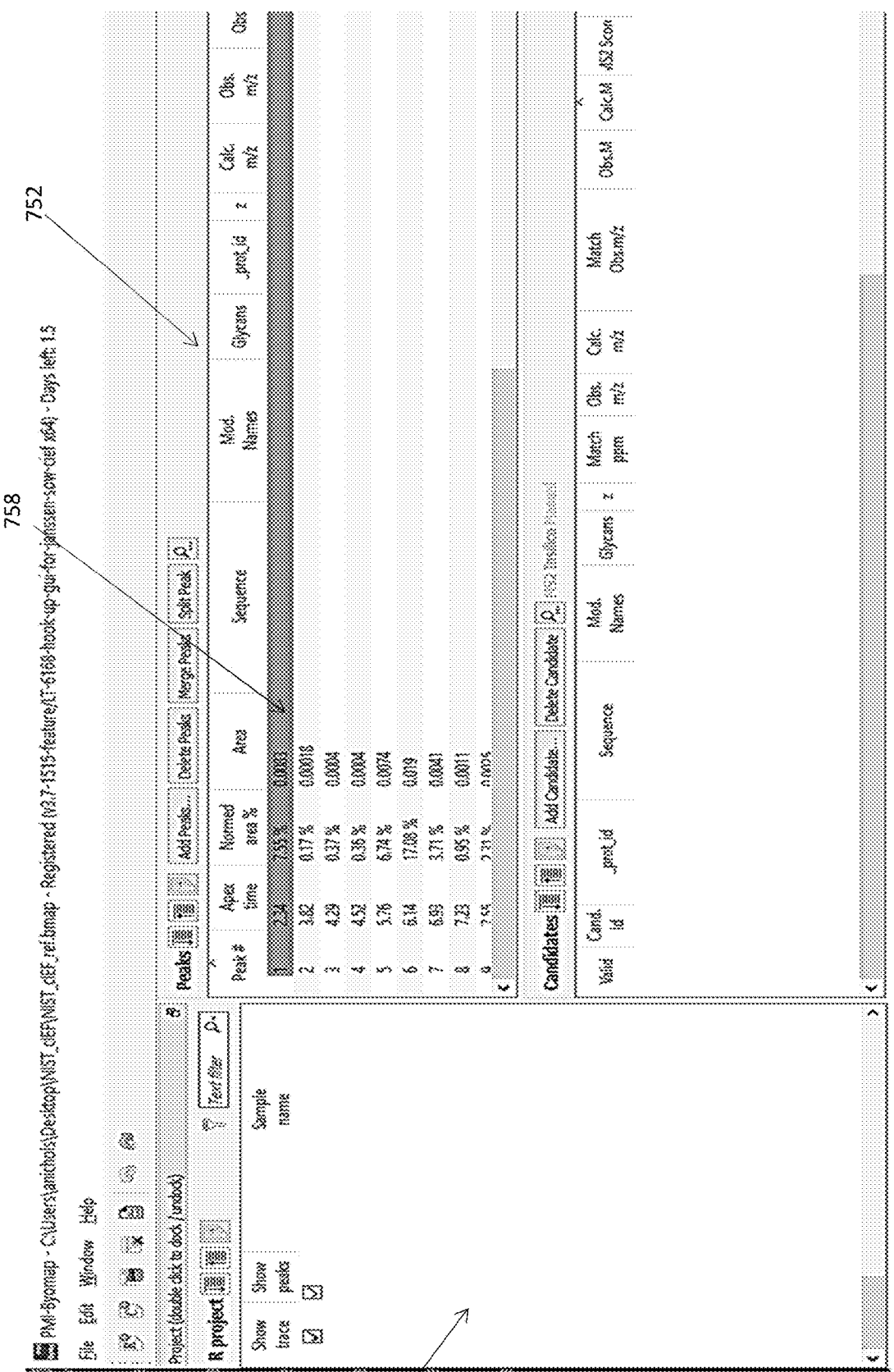
FIG. 7D(1)

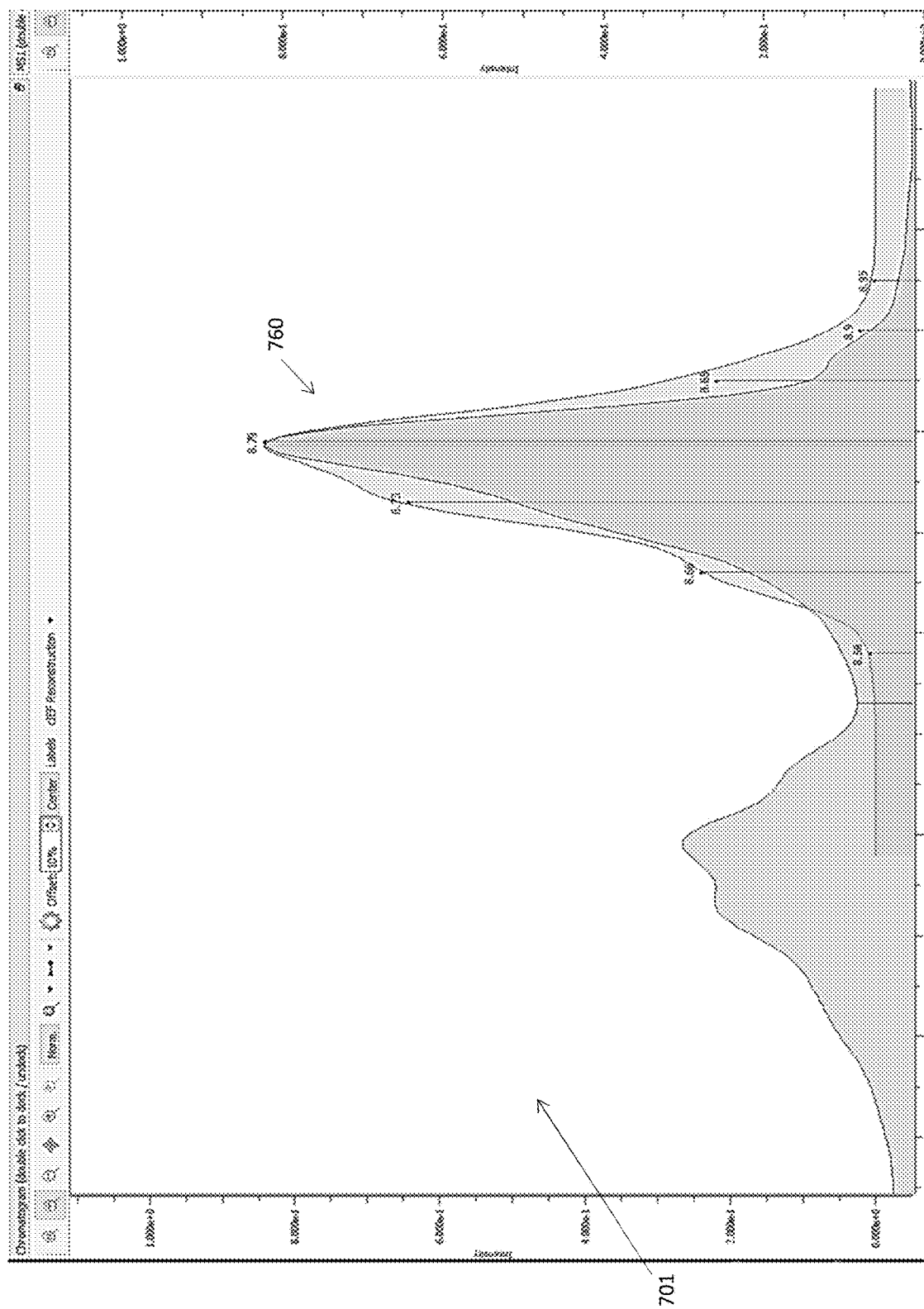
FIG. 7D(2)

PSEUDO-ELECTROPHEROGRAM CONSTRUCTION FROM PEPTIDE LEVEL MASS SPECTROMETRY DATA

CROSS REFERENCE TO RELATED APPLICATIONS

This application is a continuation of U.S. patent application Ser. No. 16/859,758, filed Apr. 27, 2020, and entitled "INTACT MASS RECONSTRUCTION FROM PEPTIDE LEVEL DATA AND FACILITATED COMPARISON WITH EXPERIMENTAL INTACT OBSERVATION," now U.S. Patent Application Publication No. 2021/0048440, which claims priority to U.S. Provisional Patent Application No. 62/839,507, filed on Apr. 26, 2019, and entitled "INTACT MASS RECONSTRUCTION FROM PEPTIDE LEVEL DATA AND FACILITATED COMPARISON WITH EXPERIMENTAL INTACT OBSERVATION," which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This invention relates to mass spectrometry (MS) data analyses of proteins, as well as associated software, graphical user interfaces and report generation.

BACKGROUND

General approaches for protein mass spectrometry include intact protein analysis and peptide-level protein analysis. Intact protein mass spectrometry, also referred to as "top-down" analysis, typically involves the use of an ion trapping mass spectrometer to store an isolated protein ion for mass measurement and multiple ion selection steps referred to as tandem mass spectrometry (MS/MS or MS2). Peptide-level protein analysis, referred to as "bottom-up" or "middle-down" analysis, involves proteolytic digestion of a protein into peptides prior to analysis by mass spectrometry, with the middle-down approach generally involving digesting the protein into larger peptides than the bottom-up approach. The peptides may be analyzed using peptide mass fingerprinting or MS/MS. In the bottom-up and the middle-down approaches, the identified peptides can be used to infer the overall protein structure.

Intact protein analysis and peptide-level protein analysis each have their advantages and disadvantages. For example, intact protein techniques may be able to capture characteristics of protein heterogeneity due to post-translational modifications (PTMs) and to detect degradation products of the protein, but may be less accurate at protein identification when there is a complex protein mixture or when the same highly abundant species is repeatedly fragmented. Bottom-up and the middle-down techniques may provide highly accurate identification of a protein even when analyzing complex mixtures, but may provide limited protein sequence coverage by identified peptides and be incapable of identifying labile PTMs. Despite the power of these techniques to identify aspects of proteins, they are not be able to resolve protein heterogeneity due to certain types of PTMs due to the complex nature of proteins and the presence of labile chemical groups.

Since some proteins, such as antibodies and recombinant proteins, are widely used for therapeutic treatment, it can be important to evaluate their heterogeneity during development, stability testing, and in quality control analyses of a product. Heterogeneity analysis and identification of the aggregates and denatured forms of proteins may also be important since these forms may be associated with an increased the risk of adverse reactions, such as allergic reactions. Therefore, it would be beneficial to provide flexible and easily implemented methods of analyzing protein mass spectra and other analytical data to elucidate the nature of protein heterogeneity due to different types of PTMs, as well as different types of protein aggregates and denatured forms of proteins.

SUMMARY OF THE DISCLOSURE

The present disclosure relates to methods an apparatuses (including devices, systems, and software, hardware and/or firmware) for analyzing mass spectrometry data related to large molecules, such as proteins. Methods described can be used to convert peptide-level mass spectrometry data of a protein or protein complex to theoretical data related to the protein or protein complex. In some embodiments, the peptide-level mass spectrometry data is used to construct a pseudo intact protein mass spectrum (also referred to as a theoretical intact protein mass spectrum or a reconstructed intact protein mass spectrum), a pseudo electropherogram (also referred to as a theoretical electropherogram or a reconstructed electropherogram) or a pseudo fluorescent labeled spectrum (also referred to as a theoretical fluorescent labeled spectrum or a reconstructed fluorescent labeled spectrum) of the protein. This theoretical data can be compared with experimentally derived data to provide information regarding possible PTMs of the protein or protein complex, which may not be attainable using experimental techniques alone. The methods can further allow a user, such as a researcher, to choose modification groups to include or exclude in generating the theoretical data, providing the user flexibility to consider various modification groups on different modified peptide forms. This may also allow the user to filter out data that is suspected as being associated with artifacts.

Also described herein are methods for reconstructing an intact mass spectrum of a protein or protein complex from peptide level data to form a pseudo intact mass spectrum of the protein or protein complex. For example a method may include: receiving mass spectrum data associated with peptides of an enzyme-digested sample of the protein or protein complex, wherein the mass spectrum data includes mass-to-charge ratio data associated with a set of modified peptide forms in the enzyme-digested sample; receiving, from a user, a selection of one or more modified peptide forms to include or to remove from the pseudo intact mass spectrum, wherein the selection is made from the set of modified peptide forms; generating the pseudo intact mass spectrum of the protein or protein complex from all or a subset of the received mass spectrum data, based on the selected one or more modified peptide forms to include or remove, wherein the pseudo intact mass spectrum is derived based in part on a comparison of the modified peptide forms to a reference list of peptide sequences; and displaying an overlay of the intact mass spectrum of the protein and the pseudo intact mass spectrum of the protein or protein complex.

The methods described herein may include comparing an intact mass spectrum of a protein or protein complex with a pseudo intact mass spectrum of the protein or protein complex. For example, a method may include: receiving mass spectrum data associated with peptides of an enzyme-digested sample of the protein or protein complex, wherein the mass spectrum data includes mass-to-charge ratio data associated with modified peptide forms in the enzyme-digested sample; generating the pseudo intact mass spectrum of the protein or protein complex from all or a subset of the received mass spectrum data, wherein a user may select one or more modified peptide forms from a set of modified peptide forms to include or to remove from the pseudo intact mass spectrum, further wherein the pseudo intact mass spectrum is derived based in part on a comparison of the modified peptide forms to a reference list of peptide sequences; and displaying an overlay of the intact mass spectrum of the protein and the pseudo intact mass spectrum of the protein or protein complex.

In some embodiments, the one or more modified peptide forms may include one or more modification groups, the one or more modification groups including one or more of a glycan group, a phosphate group, an amino group and a carboxyl group. The method can further include iteratively adjusting the displayed pseudo intact mass spectrum based on the selected one or more modified peptide forms. Iteratively adjusting the displayed pseudo intact mass spectrum can include recalculating the pseudo intact mass spectrum based on the included or removed one or more modified peptide forms. The method may further include displaying the set of modified peptide forms in a table, wherein the user may individually select the one or more modified peptide forms from the displayed set of modified peptide forms. The table may include information with regard to one or more of a corresponding protein, a position on the corresponding protein, a modification group, a modification group molecular weight, and an abundance of a modified peptide form. The intact mass spectrum can include a deconvoluted mass spectrum of the protein or protein complex. In some embodiments, the protein or protein complex includes an antibody, wherein the enzyme-digested sample includes peptides from at least a heavy chain protein and a light chain protein of the antibody. The intact mass spectrum can be an experimentally derived intact mass spectrum. The pseudo intact mass spectrum can be based on a summation of the selected one or more modified peptide forms. Displaying the overlay may include overlaying the intact mass spectrum over the pseudo intact mass spectrum, overlaying the pseudo intact mass spectrum over the intact mass spectrum, or displaying the intact mass spectrum adjacent to the pseudo intact mass spectrum. Displaying the overlay may include highlighting differences between the intact mass spectrum and the pseudo intact mass spectrum. Highlighting the differences may include displaying the intact mass spectrum and the pseudo intact mass spectrum with different colors, symbols and/or labels. Displaying the overlay may include displaying peak labels in one or both of the intact mass spectrum and the pseudo intact mass spectrum with a mass, a modification name and/or a modification group associated with a peak.

According to further embodiments, a method for generating a theoretical distribution of peptides in a protein or protein complex based on peptide-level mass spectrometry data associated with the protein or protein complex. The method can include: receiving the peptide-level mass spectrometry data including mass-to-charge ratio data associated with peptides of an enzyme-digested sample of the protein or protein complex, wherein the mass-to-charge ratio data includes data associated with modified peptide forms in the enzyme-digested sample; generating the theoretical distribution of peptides based on all or a subset of the modified peptide forms, wherein the theoretical distribution of peptides is derived based in part on a comparison of the modified peptide forms to a reference list of peptide sequences; and displaying the theoretical distribution of peptides to the user.

In some embodiments, the method further includes providing a user interface to the user that allows the user to select the subset of the modified peptide forms. The user interface may allow the user to include or to remove one or more of the modified peptide forms. The user interface include a sortable table listing the modified peptide forms. Generating the theoretical distribution of peptides may include generating a theoretical charge distribution spectrum or a theoretical fluorescent labeled spectrum. Generating the theoretical distribution of peptides may include generating a pseudo intact mass spectrum. The method can further include charge normalizing one or more modification groups that have an associated charge to generate the theoretical distribution of peptides. The method may further include displaying an experimentally derived distribution of peptides. Displaying the theoretical distribution of peptides may include displaying an overlay of the theoretical distribution of peptides and the experimentally derived distribution of peptides.

According to further embodiments, a system for generating a theoretical distribution graph based on peptide-level mass spectrometry data associated with a protein or protein complex is described. The system can include: a non-transitory computer-readable medium with instructions stored thereon, that when executed by a processor, cause the processor to: receive the peptide-level mass spectrometry data including mass-to-charge ratio data associated with peptides of an enzyme-digested sample of the protein or protein complex, wherein the mass-to-charge ratio data includes data associated with modified peptide forms in the enzyme-digested sample; generate the theoretical distribution of peptides based on all or a subset of the modified peptide forms, wherein the theoretical distribution of peptides is derived based in part on a comparison of the modified peptide forms to a reference list of peptide sequences; and display the theoretical distribution of peptides to the user. The system may further include a user interface that allows the user to select or deselect the subset of the modified peptide forms.

Also described herein are methods for reconstructing an intact mass spectrum of a protein or protein complex from peptide level data to form a pseudo intact mass spectrum of the protein or protein complex. For example a method may include: receiving mass spectrum data associated with peptides of an enzyme-digested sample of the protein or protein complex, wherein the mass spectrum data includes mass-to-charge ratio data associated with a set of modified peptide forms in the enzyme-digested sample; receiving, from a user, a selection of one or more modified peptide forms to include or to remove from the pseudo intact mass spectrum, wherein the selection is made from the set of modified peptide forms; generating the pseudo intact mass spectrum of the protein or protein complex from all or a subset of the received mass spectrum data, based on the selected one or more modified peptide forms to include or remove, wherein the pseudo intact mass spectrum is derived based in part on a comparison of the modified peptide forms to a reference list of peptide sequences; and displaying an overlay of the intact mass spectrum of the protein and the pseudo intact mass spectrum of the protein or protein complex.

Also described herein are methods for generating a theoretical electropherogram of a protein or protein complex that may include: receiving peptide-level mass spectrometry data including mass-to-charge ratio data associated with peptides of an enzyme-digested sample of the protein or protein complex, wherein the mass-to-charge ratio data includes data associated with modified peptide forms in the enzyme-digested sample; generating the theoretical electropherogram based on all or a subset of the modified peptide forms, wherein the theoretical electropherogram is derived based at least in part on a comparison of the modified peptide forms to a reference list of peptide sequences; and displaying the theoretical electropherogram to a user. Generating the theoretical electropherogram may include matching peptide sequences in the reference list of peptide sequences with peptides observed in the peptide-level mass spectrometry data. Generating the theoretical electropherogram may include predicting an abundance of each of the modified peptide forms based on a probability associated with each corresponding modified peptide form. Displaying the theoretical electropherogram may include displaying an overlay of an experimentally-derived electropherogram with the theoretical electropherogram. A peak associated with a modified peptide form having a particular pI value in the experimentally-derived electropherogram may be aligned with a peak associated with a corresponding modified peptide form with the particular pI value in the theoretical electropherogram. The one or more modified peptide forms may include one or more modification groups, the one or more modification groups including one or more of a glycan group, a phosphate group, an amino group and a carboxyl group. The method may include generating a theoretical intact mass spectrum based on all or a subset of the modified peptide forms, and displaying the theoretical intact mass spectrum to the user. The method may include displaying the theoretical electropherogram in a first window of a user interface and displaying the theoretical intact mass spectrum in a second window of a user interface.

Also described herein are methods of interactively presenting a theoretical distribution of peptides on a graphical user interface (GUI) of a computer system includes: determining, by a processor, a first theoretical distribution of peptides based on mass spectrometry data of an enzyme-digested sample of a protein or protein complex, the mass spectrometry data including mass-to-charge ratio data associated with modified peptide forms in the enzyme-digested sample, wherein the first theoretical distribution of peptides is determined based on a comparison of a first set of the modified peptide forms to a reference list of peptide sequences; displaying a graphical form of the first theoretical distribution of peptides; receiving, via the GUI, a user selection to modify the first set of the modified peptide forms to a second set of the modified peptide forms; determining, by the processor, a second theoretical distribution of peptides based on the second set of the modified peptide forms; and displaying a graphical form of the second theoretical distribution of peptides.

Any of these methods, including methods for interactively presenting a theoretical distribution of peptides on a GUI, may include displaying a table of information related to the modified peptide forms on the GUI, wherein the information includes one or more modification groups associated with each of the modified peptide forms. Receiving the user selection may include receiving a selection related to one or more of the modified peptide forms from the table of information. The table of information may include a percentage of modification associated with each of the modified peptide forms. The table of information may also or additionally include an amino acid sequence associated with each of the modified peptide forms. In some variations the method may include iteratively receiving user selections to remove or add modified peptide forms from a listing of modified peptide forms, determining, by the processor, theoretical distributions of peptides based on the user selections, and displaying the theoretical distributions of peptides in graphical form.

The first and second theoretical distribution of peptides may be displayed on the GUI. The graphical form of the first and second theoretical distribution of peptides may include one or more of a theoretical intact mass spectrum and a theoretical electropherogram. Any of these methods may include receiving, via the GUI, a user selection to display one or more of an experimentally-derived intact mass spectrum and an experimentally-derived electropherogram. For example, any of these methods may include receiving, via the GUI, a user selection to display the theoretical intact mass spectrum in an overlay view with the experimentally-derived intact mass spectrum. Displaying the overlay view may include overlaying the theoretical intact mass spectrum over the experimentally-derived intact mass spectrum or overlaying the experimentally-derived intact mass spectrum over the theoretical intact mass spectrum.

In some cases these methods may include receiving, via the GUI, a user selection to display one or more labels on or near a peak of the theoretical intact mass spectrum or the experimentally-derived intact mass spectrum. For example these methods may include receiving, via the GUI, a user selection to display the theoretical electropherogram in an overlay view with the experimentally-derived electropherogram. Displaying the overlay view may include overlaying the theoretical electropherogram over the experimentally-derived electropherogram and/or overlaying the experimentally-derived electropherogram over the theoretical electropherogram. Any of these methods may include receiving, via the GUI, a user selection to display one or more labels on or near a peak of the theoretical electropherogram or the experimentally-derived electropherogram. For example, a method may include receiving, via the GUI, a user selection to display a close-up of a particular peak on the graphical form of the first or second theoretical distribution of peptides. The GUI may be presented on a display of a remote device as part of a cloud-based or web-based system.

As mentioned, also described herein are apparatuses (e.g., systems, devices, etc.) configured to perform any of these methods. For example, described herein are systems that include one or more processors and may be configured for performing any of these methods. For example, a system for generating graphical information associated with a protein or protein complex may include: a non-transitory computer-readable medium with instructions stored thereon, that when executed by a processor, cause the processor to: receive peptide-level mass spectrometry data including mass-to-charge ratio data associated with peptides of an enzyme-digested sample of the protein or protein complex, wherein the mass-to-charge ratio data includes data associated with modified peptide forms in the enzyme-digested sample; generate a theoretical distribution of peptides based on all or a subset of the modified peptide forms, wherein the theoretical distribution of peptides is derived based in part on a comparison of the modified peptide forms to a reference list of peptide sequences; and display the theoretical distribution of peptides in graphical form. The theoretical distribution of peptides may include one or more of a theoretical electropherogram and a theoretical intact mass spectrum. The non-transitory computer-readable medium may include instructions to cause the processor to generate and display one or more of an experimentally-derived electropherogram and an experimentally-derived intact mass spectrum. Generating the theoretical distribution of peptides may include matching peptide sequences in the reference list of peptide sequences with peptides observed in the peptide-level mass spectrometry data. The non-transitory computer-readable medium may include instructions to cause the processor to generate and display a table of information related to the modified peptide forms, wherein the information includes one or more modification groups associated with each of the modified peptide forms. The table of information may include a percentage of modification associated with each of the modified peptide forms. The table of information may include an amino acid sequence associated with each of the modified peptide forms. The non-transitory computer-readable medium may include instructions to cause the processor to dynamically update the displayed theoretical distribution of peptides based on received input from a user. The received input may include instructions from the user to remove or add modified peptide forms from a listing of modified peptide forms. Displaying the theoretical distribution of peptides may include displaying an overlay including the theoretical distribution of peptides and an experimentally-derived distribution of peptides. Displaying the overlay may include displaying peak labels on or near one or more of the theoretical distribution of peptides and the experimentally-derived distribution of peptides. The system may have a cloud-based or web-based computer architecture, wherein the theoretical distribution of peptides is displayed at one or more local computers. The system may have a cloud-based or web-based computer architecture, wherein the non-transitory computer-readable medium further comprises instructions to receive multiple sets of peptide-level mass spectrometry data from multiple local computers. The system may have a cloud-based or web-based computer architecture, wherein one or more computational activities related to generating the theoretical distribution is executed at one or more local computers. The system may have a cloud-based or web-based computer architecture, wherein one or more computational activities related to generating the theoretical distribution is executed at one or more remote computers, which may be part of a distributed computing cloud-based platform.

These and other features and advantages are described herein.

Any of the apparatuses, user interfaces and methods described herein can include aspects described in U.S. Pat. No. 10,546,736, issued on Jan. 28, 2020 and entitled, "INTERACTIVE ANALYSIS OF MASS SPECTROMETRY DATA INCLUDING PEAK SELECTION AND DYNAMIC LABELING," in U.S. Pat. No. 10,510,521, issued on Dec. 17, 2019, entitled "INTERACTIVE ANALYSIS OF MASS SPECTROMETRY DATA," U.S. Pat. No. 9,640,376, issued on May 2, 2017, entitled "INTERACTIVE ANALYSIS OF MASS SPECTROMETRY DATA," U.S. Pat. No. 10,319,573, issued on Jun. 11, 2019, entitled "METHODS AND APPARATUSES FOR DETERMINING THE INTACT MASS OF LARGE MOLECULES FROM MASS SPECTROGRAPHIC DATA," U.S. Pat. No. 9,385,751, issued on Jul. 5, 2016, entitled "ENHANCED DATA COMPRESSION FOR SPARSE MULTIDIMENSIONAL ORDERED SERIES DATA," and U.S. Pat. No. 10,354,421, issued on Jul. 16, 2019, entitled "APPARATUSES AND METHODS FOR ANNOTATED PEPTIDE MAPPING," each of which is herein incorporated by reference in its entirety.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A(1) and 1A(2) schematically illustrate an example of deriving an intact mass spectrum.

FIGS. 1B(1) and 1B(2) schematically illustrate one method of generating a pseudo intact mass spectrum, as described herein.

FIG. 1C illustrates an exemplary table that may be used to derive the pseudo intact mass spectrum of FIGS. 1A(1) and 1A(2).

FIGS. 2A(1) and 2A(2) illustrate an exemplary overlay of an experimentally-derived (e.g., empirical) intact mass spectrum and a reconstructed (e.g., pseudo) intact mass spectrum and table; the table is inset as part of the image. The protein in this example is an antibody heavy chain (HC).

FIG. 2C is an example of a light chain (LC) of a second antibody (treated). FIG. 2D is an example of a heavy chain (HC) of the second antibody (treated). FIG. 2E is example of the HC of the second antibody ("wild type"). FIG. 2F is an example of the LC of the second antibody ("wildtype").

FIGS. 3A(1) and 3A(2) illustrate another exemplary overlay and table for comparing an experimentally derived intact mass spectrum with a pseudo intact mass spectrum.

FIG. 3B is a table showing details of the constituent composition.

FIGS. 7A(1) and 7A(2) illustrate an exemplary graphical user interface (GUI) for generating and analyzing theoretical peptides distributions using mass spectrometry data.

FIGS. 7D(1) and 7D(2) illustrate another aspect of the GUI of FIGS. 7A(1) and 7A(2), showing how a user can display and analyze one or more peaks in a theoretical electropherogram and/or an experimentally-derived electropherogram.

DETAILED DESCRIPTION

Figure 2B:
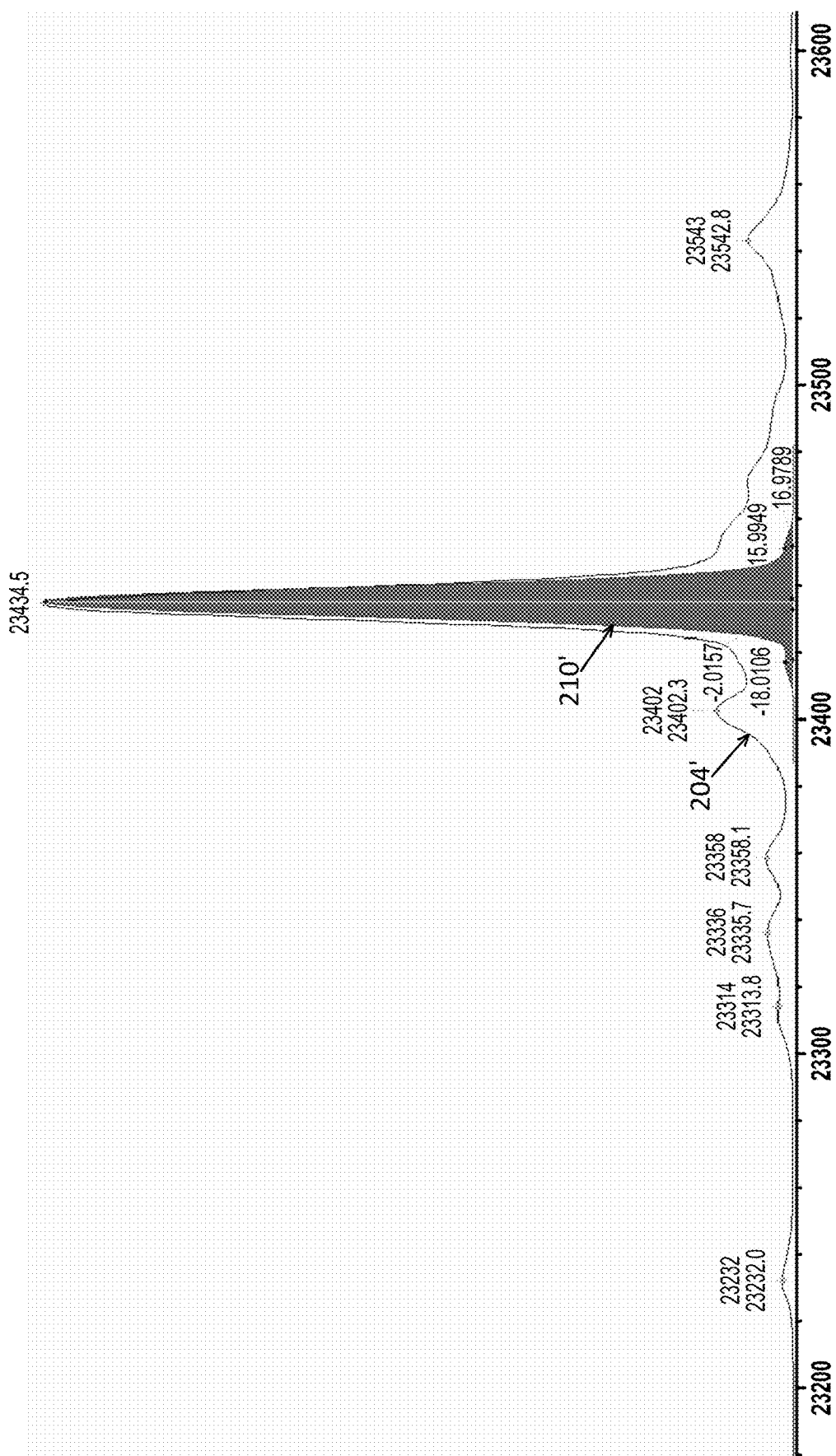
FIG. 2B shows another example of an overlay of an experimentally-derived (e.g., empirical) intact mass spectrum and a reconstructed (e.g., pseudo) intact mass spectrum. The protein in this example is an antibody light chain (LC).
Figure 2C:
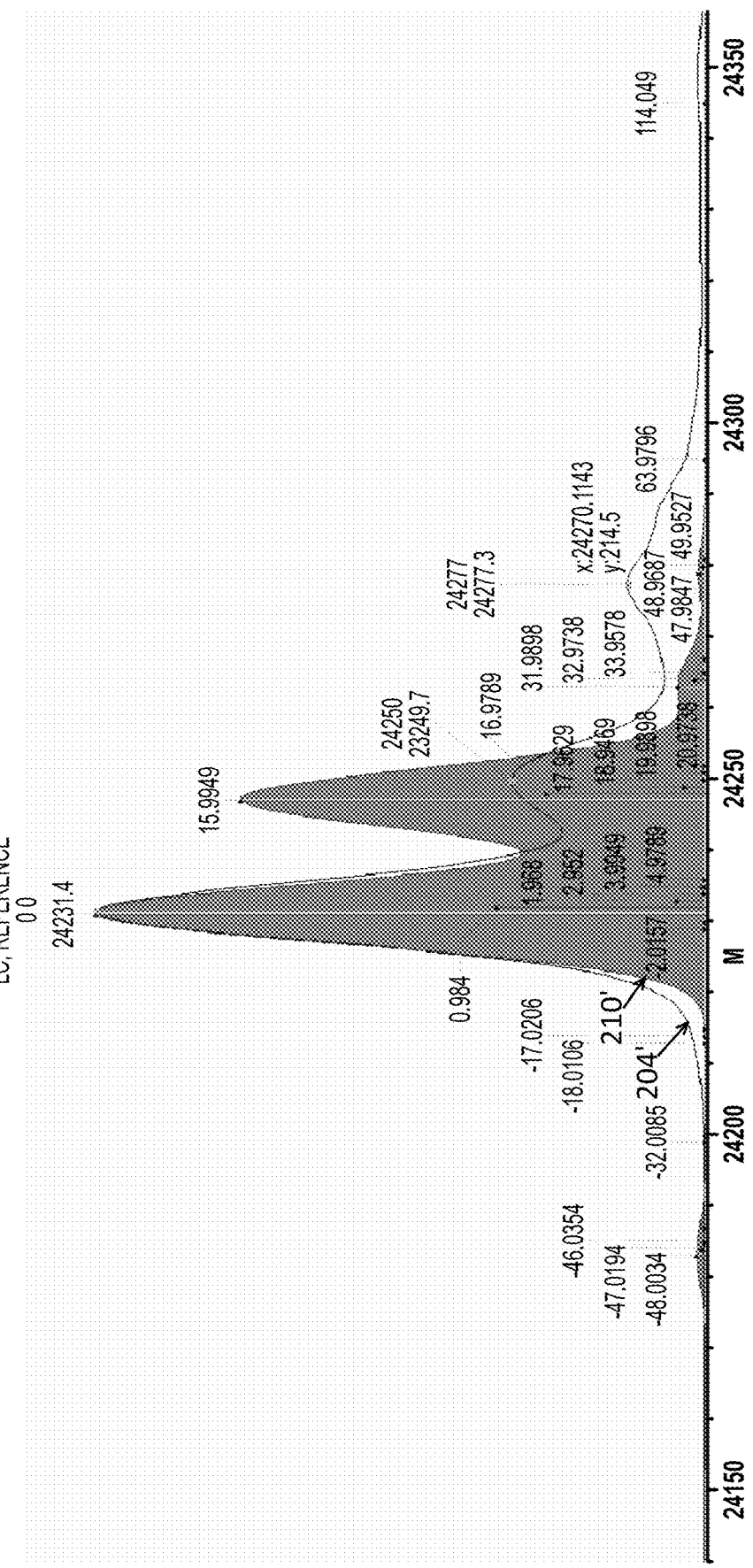
FIGS. 2C, 2D, 2E and 2F show additional examples of comparisons between experimentally-derived (e.g., empirical) intact mass spectra and reconstructed (e.g., pseudo) intact mass spectra.
Figure 2D:
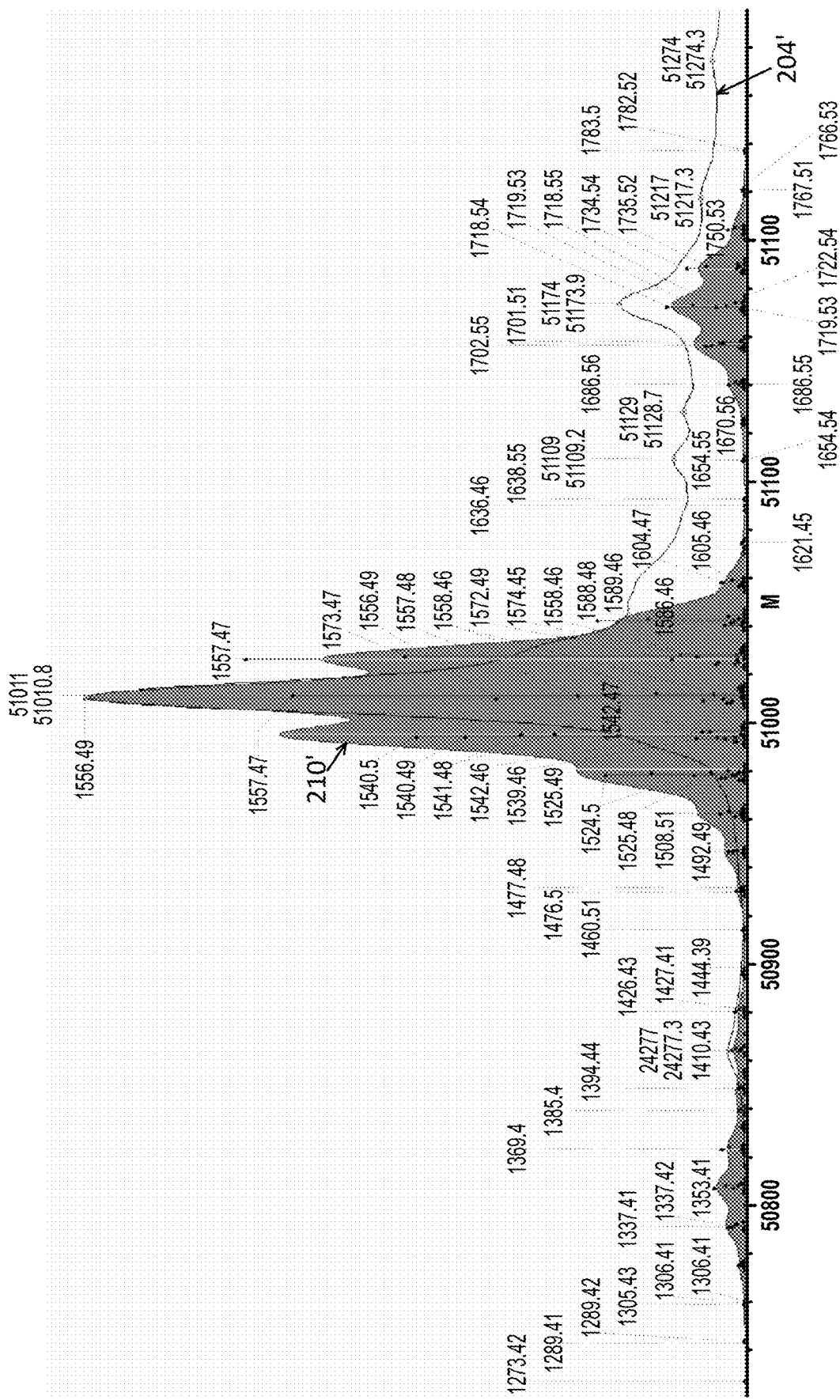
Figure 2E:
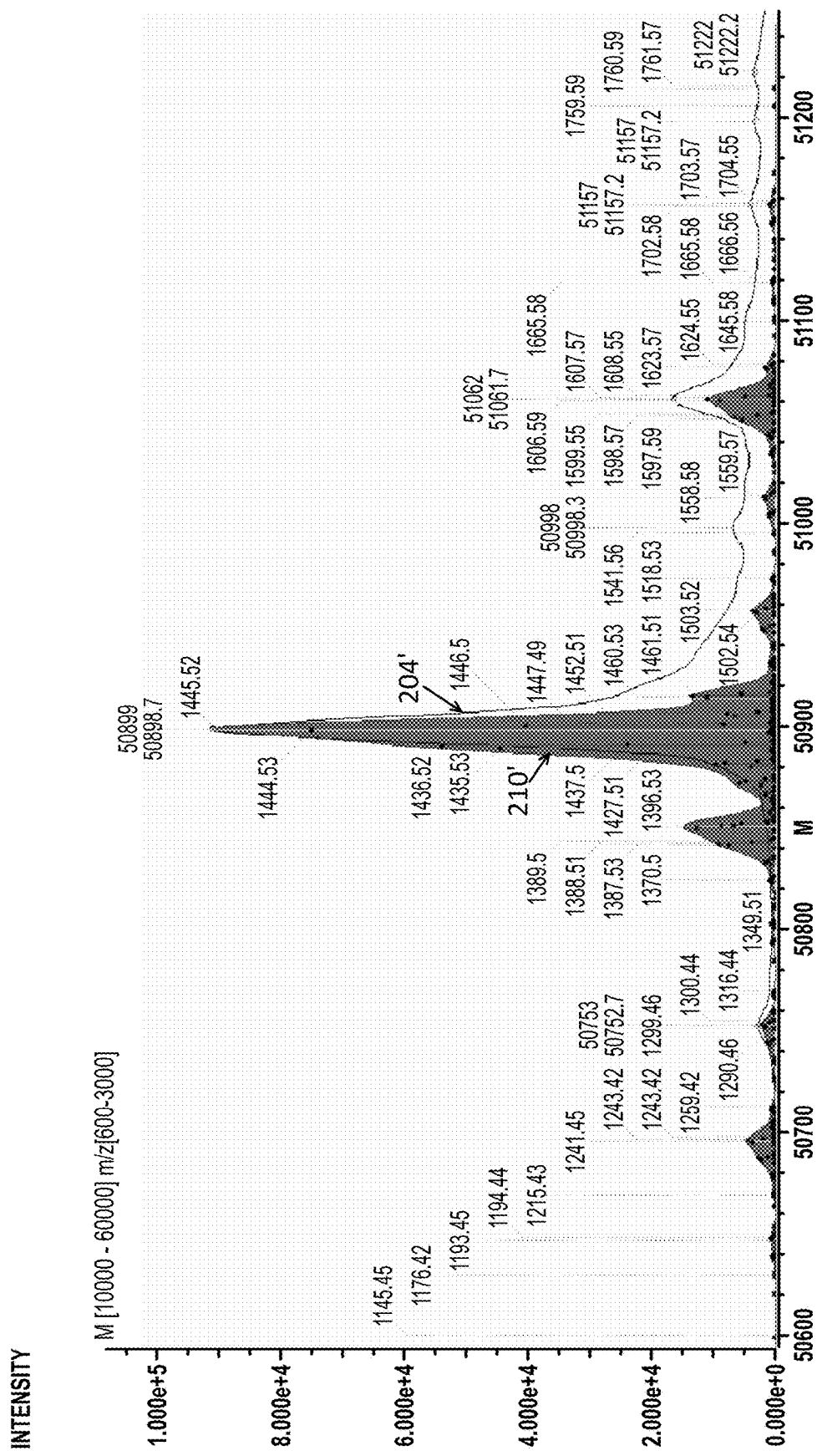
Figure 2F:
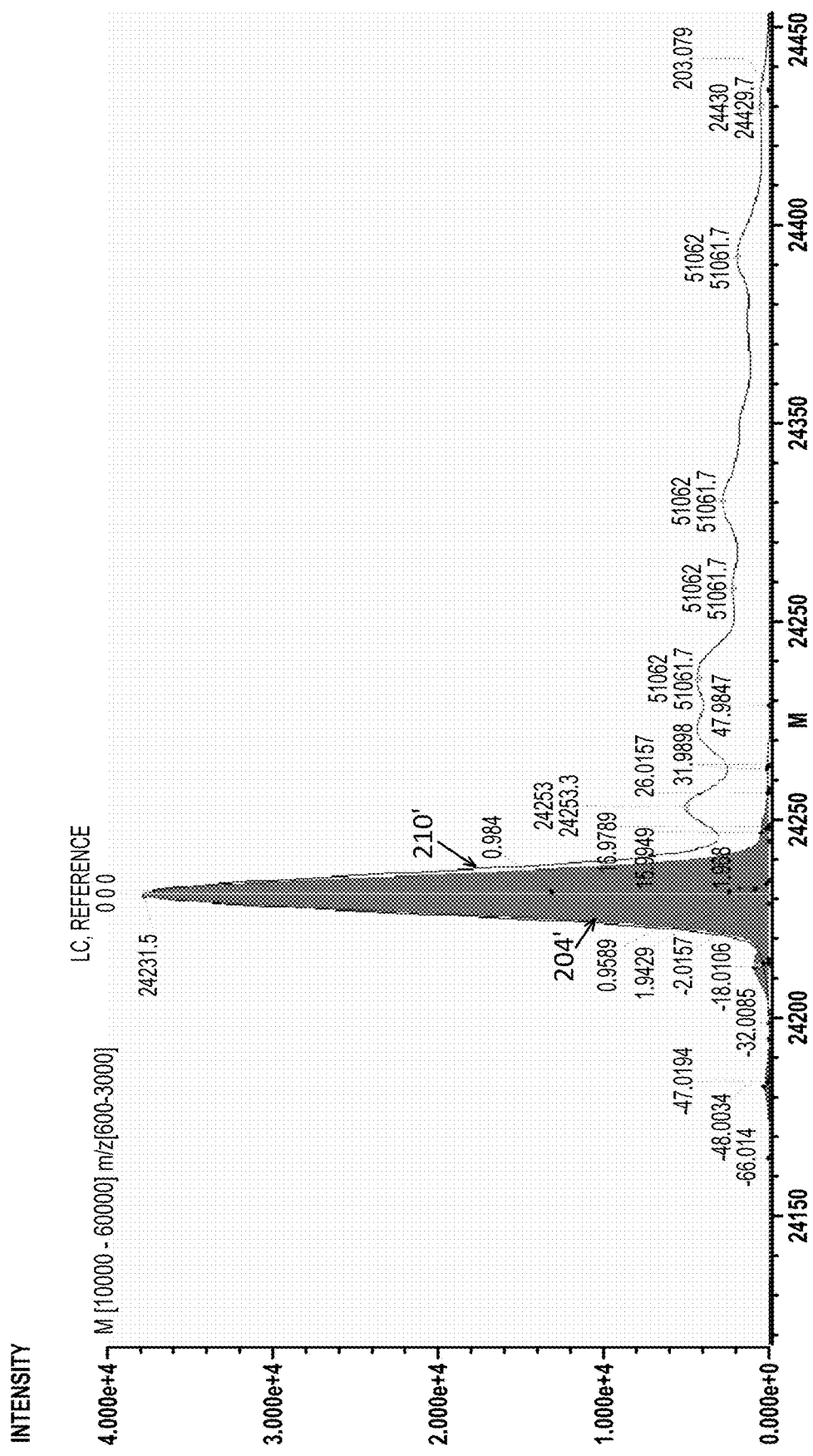

Described herein are methods and apparatuses for performing them (including devices, systems and/or machine-readable code such as software and firmware) that may allow a user to connect and compare peptide-level and intact mass data from the same sample. Based on an identified and quantified liquid chromatography mass spectrum (LCMS) features made at the peptide level, these methods and apparatuses may create a theoretical sub-unit mass spectrum, which may be referred to herein as a pseudo intact mass spectrum. The method or apparatus may facilitate a comparison between the theoretical and observed Intact Mass in a user-interactive manner that permits more accurate and reliable comparison and analysis. These methods and apparatuses described herein may also assist in generating a report that summarizes the identified masses of each.

For example, the methods and systems described herein can be used to characterize protein post-translational modifications (PTMs). PTMs refer to modifications due to the covalent addition, removal or chemical modifications to functional groups on a protein. Such modifications can occur due to phosphorylation, glycosylation, cyclization ubiquitination, nitrosylation, methylation, acetylation, lipidation, proteolysis and/or other modifications. Different PTMs can influence many aspects of normal cell biology and pathogenesis during protein biosynthesis, and are thus of great interest for scientist to identify and characterize. Therefore, identifying, characterizing and understanding PTMs dynamics can be critical in the study of cell biology and disease treatment and prevention.

Scientists often employ intact mass spectrometry analyses to characterize proteins, protein complexes and protein-related molecules since these techniques generally involve relatively limited sample preparation and provide characterization of the overall mass of the proteins, protein complexes and protein-related molecules. In the case of monoclonal antibodies (mAb), a scientist may perform a reduction to separate the heavy and light chains of the mAb or may use a simple enzyme to cleave the antigen-binding fragment (Fab) from the fragment crystallizable (Fc) region of a mAb, which are generally large molecular species. These large molecular species may be analyzed using intact mass spectrometry analyses to characterized portions of the mAb. While the intact mass spectrometry measurements can show that modifications exist, or even the prevalence of modifications, one may not be able to determine the location of modifications. The methods and apparatuses described herein may explicitly and intuitively allow a user to determine the location of such modifications.

Scientists may also employ peptide-level mass spectrometry analyses on proteins, protein complexes and protein-related molecules, where these molecules are enzymatically digested into smaller sequences of peptides before analysis by mass spectrometry. By measuring the mass of these smaller sequences of peptides, one can determine which peptides have been modified, and thus where on the original protein or complex such modifications exist. One of the disadvantages of peptide-level mass spectrometry is that sample preparation is generally more complicated, time consuming and can result in sample preparation artifacts.

Although these different types of mass spectrometry techniques are both able to characterize various aspects of molecular species, it can be difficult to directly compare their results because, for example, protein fragments and peptides sequences may have different charge states based in the analytical technique used. Thus, comparing intact mass spectrometry data with peptide-level mass spectrometry data can be like comparing apples and oranges.

The methods and systems described herein may allow one to take peptide-level analysis and convert it to one or more pseudo intact mass spectra (also referred to as theoretical intact mass spectra or intact mass spectra reconstruction). A pseudo intact mass spectrum can then be compared to experimentally observed intact mass spectra in an "apples-to-apples" fashion. This sort of comparison can be used elucidate the nature of various PTMs not observable using intact mass spectrometry or peptide-level mass spectrometry alone.

FIGS. 1A(1) and 1A(2) schematically illustrate an exemplary process for providing a pseudo intact mass spectra and comparing it with an experimentally derived intact mass spectra. One or more of the processes described with reference to FIGS. 1A(1) and 1A(2) may be implemented by a processor (e.g., one or more processors, such as a computer) and may be viewable and accessible by a user via a user interface (e.g., screen, touchscreen, etc.). Experimentally derived intact mass spectrum data from a protein sample (e.g., reduced mAb) can be collected 102 and stored. The intact mass spectrum may be deconvoluted 104, which can involve recalculating multiply-charged species into singly-charged form and grouping the singly-charged species together according to the m/z. FIGS. 1A(1) to 1B(2) illustrate a deconvoluted mass spectrum 106 of a heavy chain subunit of a mAb, with peak labels showing corresponding measured masses.

Experimentally derived protein-level mass spectrum data (MS/MS data) is also collected from a digested sample of the same protein 106 into constituent peptides, including modified (e.g., degraded) forms of the peptides. The peptide-level data can be analyzed to identify and quantify the peptides and modified peptide forms in the digested sample. This data can be stored and organized in a list or table, such as data table 108. The data can be used to construct a pseudo intact mass spectrum 110 (also referred to as a theoretical or reconstructed intact mass spectrum).

FIG. 1C shows details of the data that can be stored in data table 108 according to some embodiments. Note that the data table 108 is an example, and that the information and the order of elements provided in a data table may vary. The example data table 108 indicates the name of the protein ("Protein name"), peptide sequences in the protein having modifications ("Sequence (unformatted)"), a variable indicating a position of the modified amino acid vis-a-vis the protein ("Var Position Protein") (e.g., if the first amino acid in the protein is degraded this value will equal 1), a description and location of the modified peptide forms within the protein ("Mod Summary") (e.g., if Mod Summary is M4(Oxidation/15.999) for the peptide sequence ASCMER, it means that the amino acid in the 4th position, which is M, is modified by 15.999 Da), a description of the modified peptide forms found at the denoted residue ("Mod Name"), and values related to the quantity of the modified peptide forms in the sample.

As described herein, the modified peptide forms may be the result of be phosphorylation, glycosylation, cyclization, ubiquitination, nitrosylation, methylation, acetylation, lipidation, proteolysis and/or other post-translational modification. The modification groups may include, for example, one or more of a glycan group, a phosphate group, an amino group, a carboxyl group and other functional groups. In some cases, the modification group is an amino acid, such as a lysine group. In some cases, the addition or loss of a modification group from a peptide can result in a mass change to the peptide. Thus, the modification groups may also have an associated charge.

Quantifying the peptide-level data may involve comparing the masses of the observed peptides with a reference listing of peptides in the protein, such as a sequence database or a peptide spectral library, and predicting the abundance of the modified peptide forms based on a probability associated with each corresponding modified peptide form. For example, a reference peptide sequence, a reference standard or a reference material can be matched against the observed peptides to obtain the degree of similarity or identity of the observed peptides to map the peptides to locations in the intact protein. In some cases, this information is displayed to a user in a list or table so that the user can view the various modified peptide forms (e.g., table 108 or a simplified form of table 108). In some embodiments, the list or table includes a probability associated with each corresponding modified peptide form. In some instances, the list or table is organized such that the peptides are selectively arranged by molecular weight, peptide type or modification group type.

Returning to FIGS. 1A(1) and 1A(2), the pseudo intact mass spectrum 110 of the protein can be generating based on the data table 108. For example, the contributions of each of the identified and quantified modified peptide forms can be summed together and used to estimate what an intact mass spectrum would look like, i.e., pseudo intact mass spectrum 110. FIGS. 1A(1) and 1A(2) illustrate a pseudo intact mass spectrum 110 of the same heavy chain subunit of the mAb of the experimentally derived mass spectrum 106. As with the experimentally derived mass spectrum 106, the pseudo intact mass spectrum 110 can include peak labels showing corresponding masses associated with each peak in the spectrum.

In some embodiments, the experimentally derived intact mass spectrum 106 and the pseudo intact mass spectrum 110 are displayed in an overlay such that the user can easily compare the two spectra. For example, the intact mass spectrum 106 may be displayed over the pseudo intact mass spectrum 110 (e.g., in a single window), or the pseudo intact mass spectrum 110 may be displayed over the intact mass spectrum (e.g., in a single window). In some cases, the overlay includes a mirror graph where one of the intact mass spectrum 106 or the pseudo intact mass spectrum 110 is reflected over the x or y axis. In some embodiments, the overlay display includes a first window with the intact mass spectrum 106 adjacent to a second window with the pseudo intact mass spectrum 110. For example, the intact mass spectrum may be displayed in a first window above a second window displaying the pseudo intact mass spectrum (e.g., as shown in FIGS. 1A(1) and 1A(2)), or vice versa. In some embodiments, the first and second windows are laterally adjacent to each other. In any of the overlays, the intact mass spectrum and the pseudo intact mass spectrum may be aligned such that peaks associated with the same peptide forms are lined up with each other. The peaks may also be scaled (e.g., normalized) such that the peak intensities (e.g., corresponding to relative abundance) can be directly compared. In some cases, the peaks in one or both of the intact mass spectrum and the pseudo intact mass spectrum are labeled with the mass, modification name and/or modification group associated with a peak.

The comparison between the experimentally derived intact mass spectrum 106 and the pseudo intact mass spectrum 110 can provide valuable information with regard to possible PTMs of the protein. For example, m/z of peaks A' and B' in the pseudo intact mass spectrum 110 closely correspond to the m/z of peaks A and B, respectively, in the intact mass spectrum 106. This information may be used to validate the presence of certain PTMs associated with peaks A and B. As another example, the presence of peaks C' and D' (along the sides of peak A') in the pseudo intact mass spectrum 110 are not easily resolved in the experimental intact mass spectrum 106 but may be seen in the reconstruction 110, which may indicate that peaks C' and D' correspond to PTMs of the protein not identified by the intact mass spectrum 106 alone.

In some embodiments, differences between the intact mass spectrum 106 and the pseudo intact mass spectrum 110 can be highlighted. For example, labels for the peaks C' and D' (or the peaks themselves) may be displayed in different colors and/or fonts. In some cases, the modification groups and/or modified peptide forms in the data table 108 associated with the peaks C' and D' are displayed in a distinct color, font and/or highlight. In some cases, the intact mass spectrum 106 is subtracted from the pseudo intact mass spectrum 110 (or vice versa), and this subtracted spectrum is displayed in another window or the same window. The experimental and theoretical spectra may be displayed side-by-side, or more preferably, atop one another, in order to more specifically show and/or highlight differences.

FIGS. 2A(1) and 2A(2) show another example overlay display 200 comparing an experimentally derived intact mass spectrum with a pseudo intact mass spectrum of an antibody sample. In the example overlay 200, the pseudo intact mass spectrum 210 is indicated with a filled-in line graph, and the experimentally derived intact mass spectrum 204 is indicated with a simple (non-filled) line graph. FIGS. 2A(1) and 2A(2) also show a table 208 describing constituents of the antibody used to construct the pseudo intact mass spectrum 210. The table 208 may be generated, for example, from a raw data table (e.g., data table 108, FIGS. 1A(1), 1A(2), 1B(1), 1B(2) and 1C). In some embodiments, the table 208 is also displayed to the user, for example, in the same window as the overlay 200 or in a separate window than the overlay 200.

The overlay 200 indicates similarities between the pseudo intact mass spectrum 210 and the experimentally derived intact mass spectrum 204. For example, peaks 230' and 232' in the pseudo intact mass spectrum 210 closely match peaks 230 and 232 in the experimental intact mass spectrum 204 with regard to m/z and amplitude (abundance). These similarities can be used, for example, to verify that the peaks in the experimental intact spectrum 204 correspond to certain PTMs in the protein. The overlay 200 also indicates some differences between the pseudo intact mass spectrum 210 and the experimental intact mass spectrum 204. For example, peak 234' in the pseudo intact mass spectrum 210 has a smaller amplitude than corresponding peak 234 in the experimental intact mass spectrum 204. Additionally, the pseudo intact mass spectrum 210 indicates the presence of peaks 228' and 236' with no corresponding peaks in the experimental intact mass spectrum 204. Further, the experimental intact mass spectrum 204 indicates the presence of peaks 238 and 240 with no corresponding peaks in the pseudo intact mass spectrum 210. These types of differences can be explored further by the user to estimate, for example, whether the peaks in the spectra correspond to PTMs in the protein or are related to artifacts. FIG. 2B shows another example of an overlay of a pseudo intact mass spectrum 210' and an experimental intact mass spectrum 204'. FIGS. 2C, 2D, 2E and 2F show additional examples of comparisons between experimentally-derived (e.g., empirical) intact mass spectra 204' and reconstructed (e.g., pseudo) intact mass spectra 210'.

Table 208 can list the protein ("Protein") or proteins of the sample that has/have modifications; in this case a heavy chain (HC) or light chain (LC) portion of the antibody. Table 208 can also provide the position ("Position") on the protein in which a modification is located. For example, a Position "4" on a Protein "LC" can indicate that the modification is located on the amino acid in the 4th position of a light chain portion of the antibody. Table 208 can also provide a name ("Mod") for each of the modification groups in the sample. For example, "M4(Oxidation/15.999)" can represent a modification to the amino acid in the 4th position by 15.999 Da molecular weight species due to oxidation. Table 208 can also provide a probability value ("LonelySample") indicating a relative probability or abundance of the particular modification. In some cases, the probability values can be marked by their magnitudes, using a heat map. In some embodiments, the columns of the table 208 may be sortable. For example, the user may be able to click on one of the columns "Protein", "Position", "Mod", and "LonelySample" to organize the values in the table based in ascending or descending order of the values in the selected column. Other information that may be provided in a table displayed to a user can include a "Mass Delta" value indicating a change in mass due to removal or addition of a modification group. Thus, in some embodiments, the table can include information with regard to one or more of a corresponding protein, a position on the corresponding protein, a modification group, a modification group molecular weight, and an abundance of a modified peptide form.

In some embodiments, the table 208 is configured to allow the user to select and/or deselect one or more modified peptide forms for generating the pseudo intact mass spectrum 210. For example, one or more of the lines of table 208 may be selectable by clicking on the one or more lines, or on one or more option buttons (e.g., check box or radio button) adjacent to the line(s). The selected modified peptide form(s) may be then used to generate the pseudo intact mass spectrum 210, i.e., without contribution from the unselected or deselected modified peptide form(s). In some embodiments, the table 208 can be used to filter out or include the effects of certain types of modification group(s). For example, modifications that affect the charge of a peptide (e.g., deamidation) can be included or excluded from the pseudo intact mass spectrum 210 to elucidate various effects of these types of modifications. In some cases, one or more of the modified peptide form(s) that are suspected as being artifact(s) can be deselected to filter out such artifacts.

The displayed pseudo intact mass spectrum 210 can be iteratively adjusted based on the user's selections. For instance, the user may further choose to include and/or exclude one or more modified peptide forms from the table 208, causing the pseudo intact mass spectrum 210 to be recalculated based on the updated selection. In some embodiments, the pseudo intact mass spectrum 210 is updated dynamically. In one example, the user may select/deselect one or more modified peptide forms and the pseudo intact mass spectrum 210 may be automatically updated (e.g., in real time). The selection/deselection can cause one or more of the peaks in the pseudo intact mass spectrum 210 to increase or decrease in amplitude. Thus, a user may be able to easily identify whether certain modified peptide forms are likely associated with certain protein modifications.

In some cases the user may select or deselect one or more modified peptide forms based on information provided by the experimental intact mass spectrometry data. FIGS. 3A(1) and 3A(2) are provided to illustrate one such example. FIG. 3B is a table showing details of the constituent composition (truncated). FIGS. 3A(1) and 3A(2) show a table 308 indicating modified peptide forms in a protein sample and an overlay 300 comparing the pseudo intact mass spectrum (filled-in line graph) with an experimental intact mass spectrum (simple line graph). The user noticed that the "OGlyan/1095.3966" modification (oxygen linked glycan group at 29th position) does not appear in the experimental intact mass spectrum because the glycan group is nitrogen linked, and has thus removed the "OGlyan/1095.3966" modification from the table 308. The pseudo intact mass spectrum is then recalculated based on the updated table 308 to provide an updated pseudo intact mass spectrum shown in the overlay 300, which closely matches the experimental intact mass spectrum.

Figure 4:
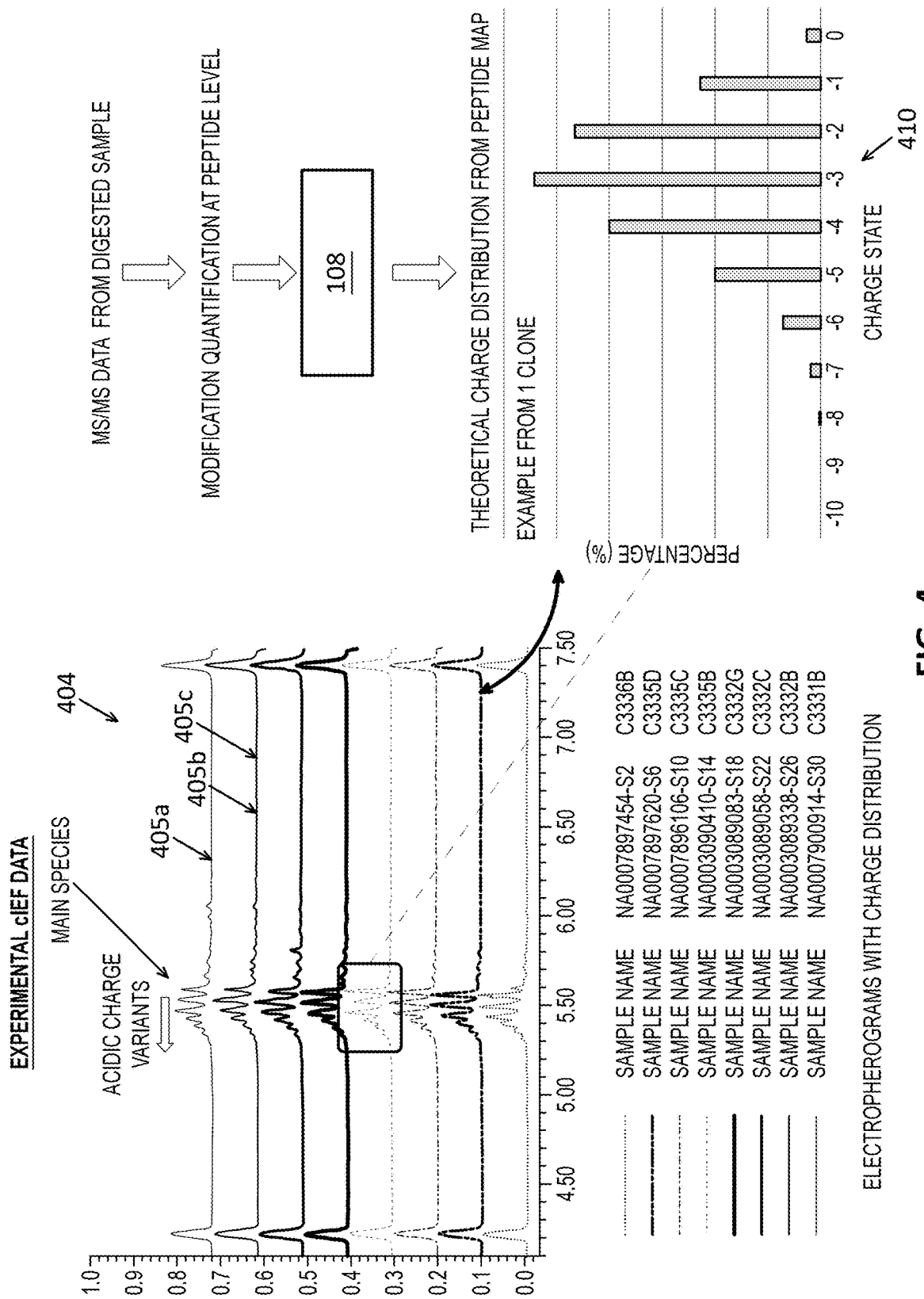
FIG. 4 illustrates a comparison of peptide map data with capillary isoelectric focusing (ciEF) data.

According to some embodiments, the peptide-level mass spectrometry data (e.g., from data table 108) can be used to generate a theoretical (or pseudo) charge distribution spectrum. FIG. 4 illustrates an exemplary process for providing a charge distribution and comparing it with experimentally derived electropherograms. Charge distribution data associated with a protein, such as capillary isoelectric focusing (ciEF) electropherogram data 404, can be received and stored. In the case of ciEF data, the peptides are distributed based on their charge states and their isoelectric points (pI). FIG. 4 shows a number of electropherograms (e.g., 405a, 405b and 405c) of a portion of mAb taken using ciEF.

Peptide-level mass spectrometry data (e.g., data table 108) of identified and quantified modified peptide forms can be used to generate a pseudo electropherogram 410 indicating the charge state of the modified peptide forms and their relative abundance. In order to generate the pseudo electropherogram 410, a charge normalization procedure may be performed. Some types of modifications (e.g., deamidation, loss of lysine or cyclization) can be associated with a charge change on a peptide. Charge normalization can involve normalizing such modification groups so that they can be compared to modification groups that do not have an associated charge. The charge normalization may also take into account charge differences at different pH levels due to zwitterions. For example, the charges may be normalize based on pI of the zwitterions. The charged normalized peptide-level data can then be used to generate the pseudo electropherogram 410 based on different charge states of the peptide forms. This pseudo electropherogram 410 may be further normalized so that it can be directly compared to the experimental electropherogram data 404. As shown in FIG. 4, the peak distribution and amplitudes of the pseudo electropherogram 410 closely match the peak distribution and amplitudes of the experimental electropherogram data 404, thus confirming the presence of certain modified peptide forms in the protein or protein complex.

In some embodiments, the pseudo electropherogram 410 and one or more of the experimental electropherograms (e.g., 405a, 405b and 405c) is displayed in an overlay. The overlay may display the pseudo electropherogram 410 over the one or more experimental electropherograms (e.g., in a single window), or the one or more experimental electropherograms may be displayed over the pseudo electropherogram 410 (e.g., in a single window). In some instances, the one or more experimental electropherograms are used together to form a single (e.g., averaged) charge electropherogram. In some cases, the overlay includes a mirror graph where one of the pseudo electropherogram 410 or the one or more experimental electropherograms is reflected over the x or y axis. In some embodiments, the overlay display includes a first window with the one or more experimental electropherograms adjacent to a second window with the pseudo electropherogram 410. For example, the one or more experimental electropherograms may be displayed in a first window laterally adjacent a second window displaying the pseudo electropherogram 410 (e.g., as shown in FIG. 4, or vice versa. In some embodiments, the first and second windows are vertically adjacent to each other. In any of the overlays, the one or more experimental electropherograms and the pseudo electropherogram 410 may be aligned such that peaks associated with the same peptide forms are lined up with each other. The peaks may also be scaled (e.g., normalized) such that the peak intensities (e.g., corresponding to relative abundance) can be directly compared. In some cases, the peaks in one or both of the one or more experimental electropherograms and the pseudo electropherogram 410 are labeled with the mass, modification name and/or modification group associated with a peak.

In some embodiments, the pseudo electropherogram 410 can be iteratively adjusted based on the user's selections. For instance, the user may choose to include and/or exclude one or more modification groups (e.g., from data table 108), causing the pseudo electropherogram 410 to be recalculated based on the updated selection. In some embodiments, the pseudo electropherogram 410 is updated dynamically (e.g., in real time).

In some embodiments, the charge distribution data shown in FIG. 4 can be used in conjunction with mass spectrometry data. Charge distribution data may be less prone to errors (e.g., having false peaks) due to artifacts compared to mass spectrometry data. Thus, comparing charge distribution data with m/z data may further confirm or dispute the presence of certain modification on proteins. In some embodiments, the charge distribution data is displayed in the same window(s) or different window(s) as the mass spectrometry data. For example, one or more of the experimental electropherogram 404, pseudo electropherogram 410, experimental intact mass spectrum 104, and pseudo intact mass spectrum 110 may be presented individually or simultaneously and/or in a single window or multiple windows. The user may be able to select and/or deselect one or more modified peptide forms (e.g., from data table 108) to observe how the peaks in the pseudo intact mass spectrum 110 and pseudo electropherogram 410 change. In some embodiments, the ciEF is presented such that the x-axis of the electropherogram is normalized based on isoelectric point (pI), such as shown in the examples of FIGS. 7A(1)-7E. The isoelectric point (pI) refers to the pH at which a molecule carries no net electrical charge or is electrically neutral in the statistical mean.

In general, the methods described herein can involve using peptide-level mass spectrometry data to generate and/or verify any type of theoretical data, and are not limited to generating a pseudo intact mass spectrum (e.g., FIGS. 1A(1)-3) or pseudo electropherogram (FIGS. 4 and 7A(1)-7E). The methods can be used to generate any of a number of types of data distributions related to the whole protein or protein complex. In one example, the peptide-level mass spectrometry data can be used to generate a theoretical fluorescent labeled protein spectrum showing the relative abundance of modified peptide forms (e.g., glycopeptides) based on observed fluorescence wavelengths.

Figure 5:
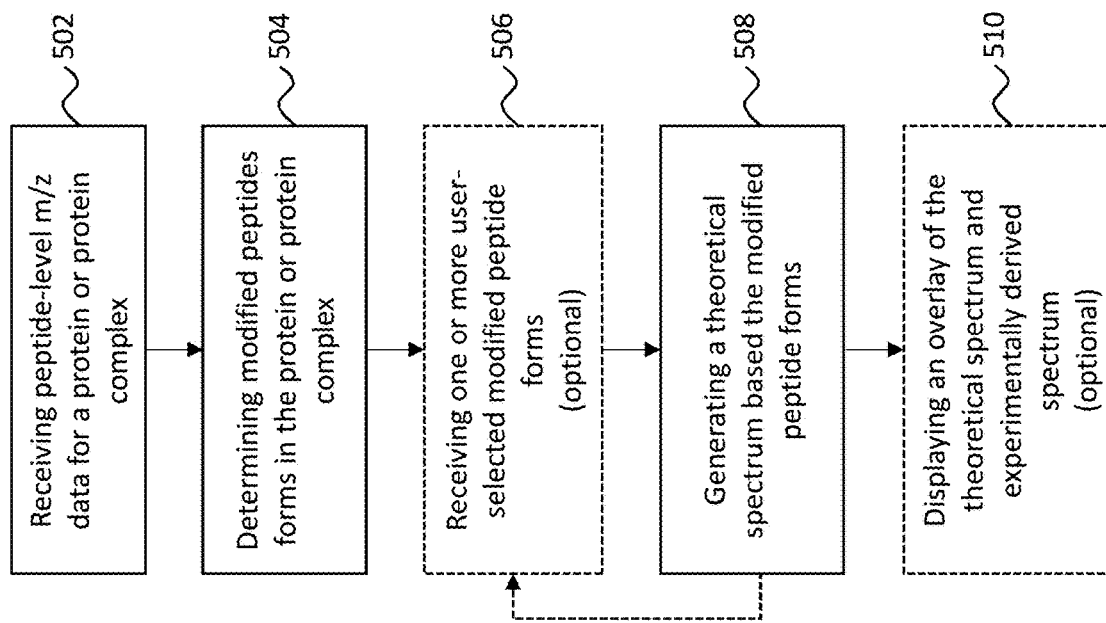
FIG. 5 illustrates flowchart indicating an exemplary process for comparing experimentally derived data with theoretically derived data based on peptide-level mass spectrometry data.

FIG. 5 shows a flowchart of an exemplary process for generating theoretical data based on peptide-level mass spectrometry data associated with a protein or protein complex. At 502, peptide-level mass-to-charge data associated with modified peptide forms of the protein or protein complex. The peptide-level data may be stored, for example, in a computer database. The mass-to-charge data may be derived from any type of mass spectrometry techniques, such as peptide mass fingerprinting or tandem mass spectrometry (MS/MS). At 504, the peptide-level m/z data is analyzed to determine the peptide constituency of the protein or protein complex, including those peptides having modification groups. Modification groups can include, for example, one or more glycan groups, phosphate groups, amino groups and/or carboxyl groups. The modified peptide forms can be identified and quantified. In some cases, a charge normalization procedure is performed to take into consideration modification groups having different charges. At 506, one or more user-selected modified peptide forms can optionally be received, such as from a user interface. At 508, a theoretical spectrum can be generated based on the modified peptide forms. The theoretical spectrum may be displayed to a user in a list (e.g., table) and/or a graph. In some embodiments, the graph illustrates a theoretical distribution of various modified peptide forms of the protein or protein complex. In some embodiments, the modified peptide forms are user selected, and the theoretical spectrum may be interactively adjusted based on input from the user. In some cases, this adjustment is done dynamically such that the user can view changes in real time. At 510, the theoretical spectrum and one or more experimentally derived spectra are optionally displayed in an overlay for the user.

Figure 6:
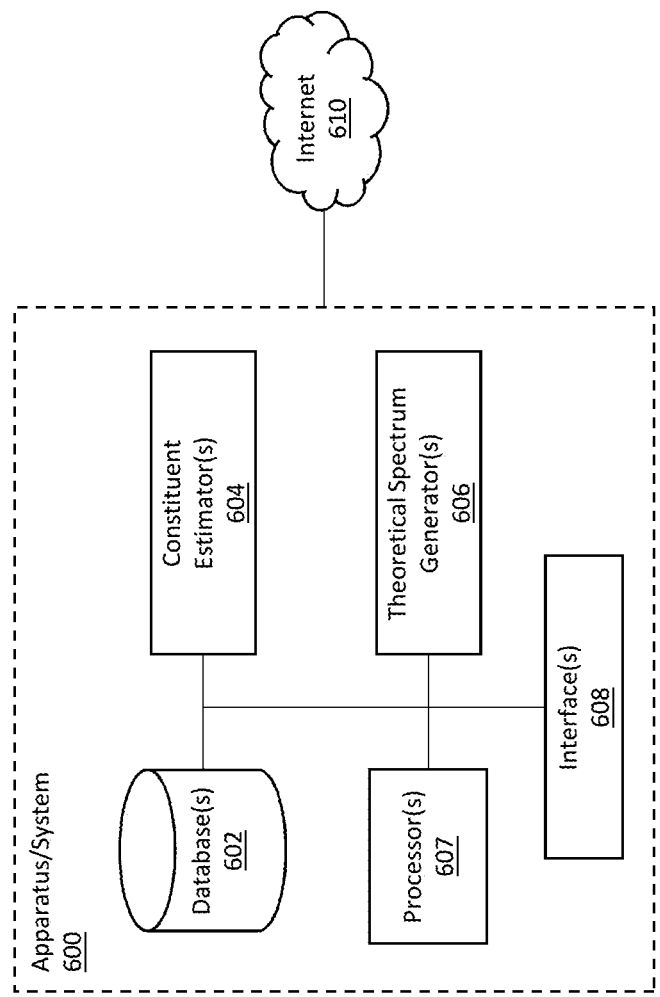
FIG. 6 illustrates an exemplary apparatus or system for generating and comparing theoretically derived data based on peptide-level mass spectrometry data.

FIG. 6 shows an example apparatus or system 600 for generating, and optionally comparing, a theoretical spectrum based on peptide-level mass spectrometry data. The apparatus or system 600 may be a stand-alone computer or may be part of a larger computer system or apparatus. The peptide-level mass-to-charge ratio (m/z) data related to a digested sample of a protein or protein complex of interest can be received by one or more interfaces 608, which may include or be operationally coupled to a computer or separate storage device (e.g., hard drive). In some cases, the interface(s) 608 is configured to receive and/or send data as part of a computer network (e.g., internet and/or intranet). The interface 608 may be configured to receive input, such as raw m/s spectrum data (e.g., via a computer file) and/or keyboard input from a user. The m/z data can be stored on one or more databases 602. The database(s) 602 may also be configured to store experimentally derived data related to the protein of interest, such as experimental intact protein m/z data, charge distribution (e.g., ciEF) data and/or florescent labeled data.

One or more constituent estimators 604 can use one or more processors 607 to estimate the peptide composition, including peptides having modification groups, and relative abundance of the peptides in the peptide-level sample. In some cases, the peptide composition and relative abundance is provided as a list (e.g., table) to the user via the interface(s) 608, which may include or be operationally coupled to one or more displays or printers. One or more theoretical spectrum generators 606 can use the processor(s) 607 to generate one or more theoretical spectra based on the estimated peptide composition and relative abundance. The theoretical spectrum generator(s) 606 may compare the observed peptides with a reference listing of peptides in the protein, such as a sequence database or a peptide spectral library, stored on the database(s) 602. The one or more theoretical spectra can be displayed on a computer screen and/or printed via the interface(s). In some embodiments, the theoretical spectrum generator(s) 606 generates the one or more theoretical spectra based on user-selected modified peptide forms received by the interface(s) 608. For example, the interface(s) 608 can include or be operationally coupled to keyboard and/or touch screen that the user may enter data. In some embodiments, the theoretical spectrum generator(s) 606 is configured to provide an overlay of the one or more theoretical spectra with one or more experimentally derived spectra.

The apparatus or system 600 may include or be part of a cloud-based or web-based platform configured for access over the internet 610. In some embodiments, a user may be able to remotely access any of the user interfaces described herein on a web browser or application installed on one or more internet-connected local devices (e.g., desktops and/or mobile devices). A user may be able to enter data (e.g., raw mass spectrum data) at a local device and view graphs on the user interface on the local device. The system may be configured to display data, such as calculated data or graphically rendered data (e.g., theoretical and/or experimentally-derived intact mass spectra and/or electropherograms) on a local device. The system may be configured to receive data from multiple local devices and/or display data at multiple local devices. For example, the system may allow multiple users to simultaneously create, view, edit, annotate, store, share and otherwise manage content in real time or near real time. The platform may have a high-availability architecture suited for handling a large volume of user requests. One or more computational activities related generating output (e.g., theoretical and/or experimentally-derived intact mass spectra and/or electropherograms) may be executed at one or more local computers or executed at one or more remote computers. Data (e.g., raw MS data, calculated data) may be stored at one or more local servers (e.g., computers) or executed at one or more remote servers (e.g., computers). The remote servers (e.g., computers) may be one or more servers at one location or as part of a distributed computing cloud-based platform. In some embodiments, the data may be cached locally (e.g., at the local device(s)). In some cases, the user at a local device can access a wide range of services such as storage, application development platforms and/or on-demand computing cycles. In some embodiments, the cloud-based or web-based platform is an enterprise platform to provide services to an organization or business. In some embodiments, the cloud-based or web-based platform is configured to analyze and systematically extract information from large data sets (e.g., big data).

FIGS. 7A(1)-7E show an example graphical user interface (GUI) for generating and analyzing theoretical peptides distributions using mass spectrometry data. FIGS. 7A(1) and 7A(2) show the user interface displaying a project window 750 and a chromatogram window 701. In some embodiments, the user interface may display one or more additional or alternative windows. For example, the user interface may additionally or alternatively display an intact mass spectrum window displaying one or more intact mass spectra, such as any of the theoretical and/or experimentally-derived intact mass spectra, such as described above. Each of the windows (e.g., chromatogram window 701 or project window 750) may be docked (viewed) or undocked (removed) from the user interface. In some embodiments, the windows may be docked and undocked by double clicking the window of interest or an icon/text associated with the window of interest. Any of the windows may function as a pop-up window and/or may be moveable in the user interface by the user.

The project window 750 can include information regarding one or more analysis projects. Each of the analysis projects can have data related to one or more target proteins and/or one or more mass spectroscopy raw data files. The project window 750 can include a number of sub-windows. The example shown includes an R project window 751, which lists the Sample Names of each project and options to show the trace and/or peaks in the reconstructed graphs/spectra. A Peaks sub-window 752 can list peak related information such as Peak number, Apex time, Normed area %, Area, Sequence, Modification Name, Glycans, protein ID, z (charge), calculated m/z, Observed mass, Calculated mass, candidate ID, Start time, End time, and Sample ID. A Candidates sub-window 753 can list the protein candidates used in the reconstruction calculation, where candidates may be added or removed based on user input. A Protein Coverage sub-window 754 can provide information related to the number of amino acids in a specific peptide sequence found in the peptides sequenced in the MS/MS project. The Protein Coverage sub-window 754 can include a list the peptide sequences of selected proteins, along with a calculated a Coverage summary and Coverage percent %.

The chromatogram window 701 can display one or more experimentally-derived electropherograms and/or one or more theoretical electropherograms. In the example shown, the chromatogram window 701 displays an overlay view of an experimentally-derived electropherogram 704 and a theoretical electropherogram 710. In the example electropherogram shown, the charges of the molecular species are normalized so that species with different isoelectric points (pIs) are distributed along the x-axis. An overlay view allows the user to compare peaks within the theoretical electropherogram 710 with corresponding peaks in the experimentally-derived electropherogram 704. The experimental electropherogram 704 may be displayed using a first display characteristic (e.g., a first color, shading, line thickness and/or labeling) compared to a second display characteristic (e.g., a second color, shading, line thickness and/or labeling) of the theoretical electropherogram 710 that may be different than the first display characteristic.

Figure 7B:
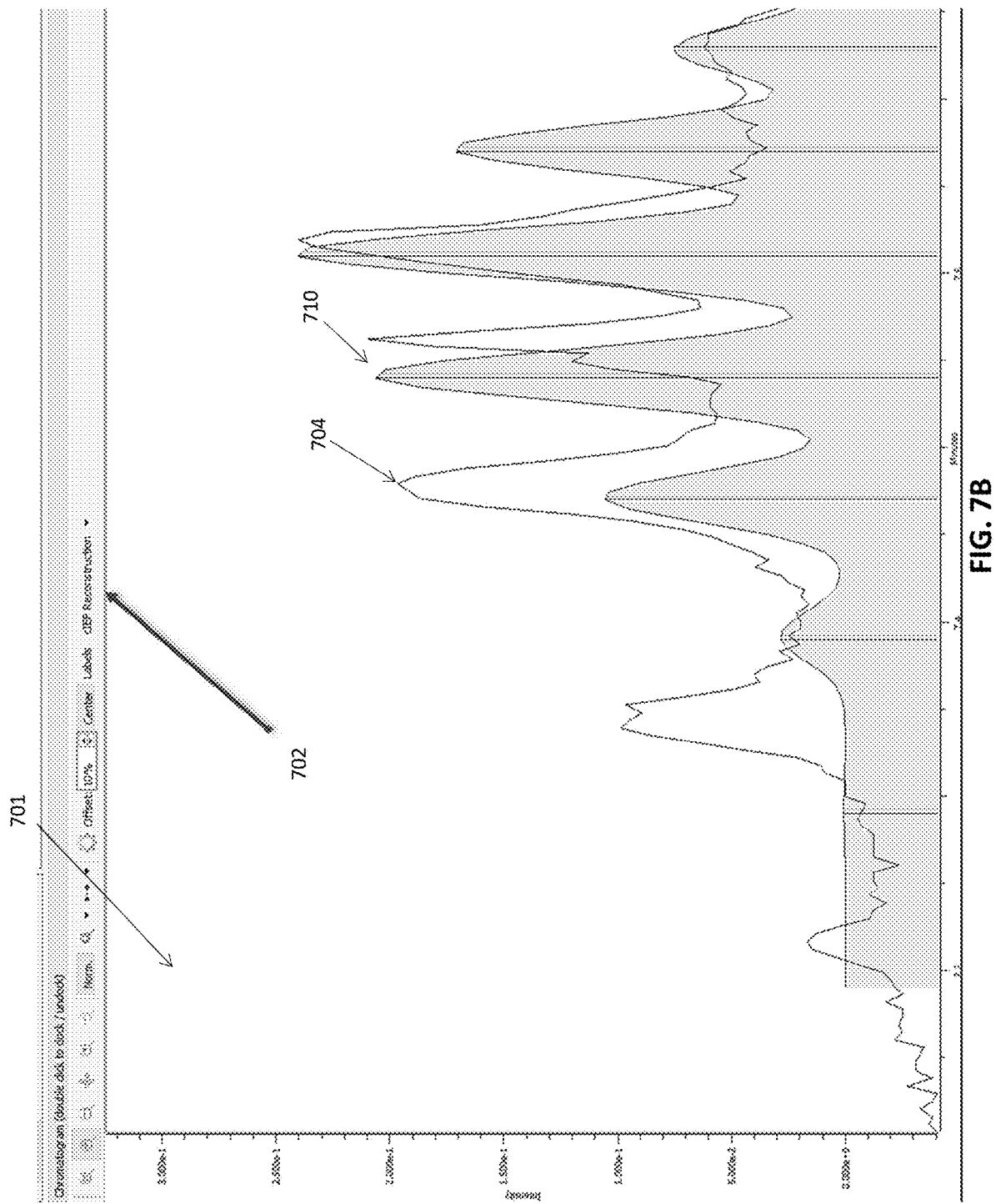
FIG. 7B illustrates an aspect of the GUI of FIGS. 7A(1) and 7A(2), showing a close-up view of an overlay view of a theoretical electropherogram and an experimentally-derived electropherogram in a window of the GUI.
Figure 7C:
FIG. 7C illustrates another aspect of the GUI of FIGS. 7A(1) and 7A(2), showing a listing of modified peptide forms used in forming theoretical electropherogram in another window of the GUI.

FIG. 7B shows a close-up view of a portion of the chromatogram window 701 of FIGS. 7A(1) and 7A(2), showing how the user interface can be used to reconstruct or modify the theoretical electropherogram 710. The chromatogram window 701 can include a user interface control element 702 (e.g., button, dropdown menu, switch, toggle, tab, slider or icon) that provides access to a Reconstruction window such as shown in FIG. 7C. The Reconstruction window (e.g., FIG. 7C) can include a list 720 of peptide forms identified in the mass spectrometry data, including a protein name, protein position, modification name, and modification percent. Each of the proteins listed in the list 720 may be selectable for removal, for example, using a remove row button 723). The user interface can allow a user to add one or more peptide forms to the list 720, for example, using an add row button 724. The theoretical electropherogram 710 can be updated (e.g., automatically and/or dynamically) based on the user selected peptide forms. The user interface may allow a user to import information related to one or more proteins (e.g., additional raw mass spectroscopy data) using, for example, an import button 725. The Reconstruction window can also include a list of target proteins 722, including the protein name, protein count, protein Gauss width, and protein mass offset. Target proteins may be added and/or removed from the list of target proteins 722 using, for example, an add row button 726 and a remove row button 727.

FIGS. 7D(1) and 7D(2) illustrate how a user can display and analyze a particular peak in the chromatogram window 701. In the Peaks sub-window 752, the user may select a row 758 corresponding to a particular peak in the ciEF electropherogram to cause the selected peak to be displayed in the electropherogram in the chromatogram window 701. In some cases, the user may be able to zoom in on the selected peak.

Figure 7E:
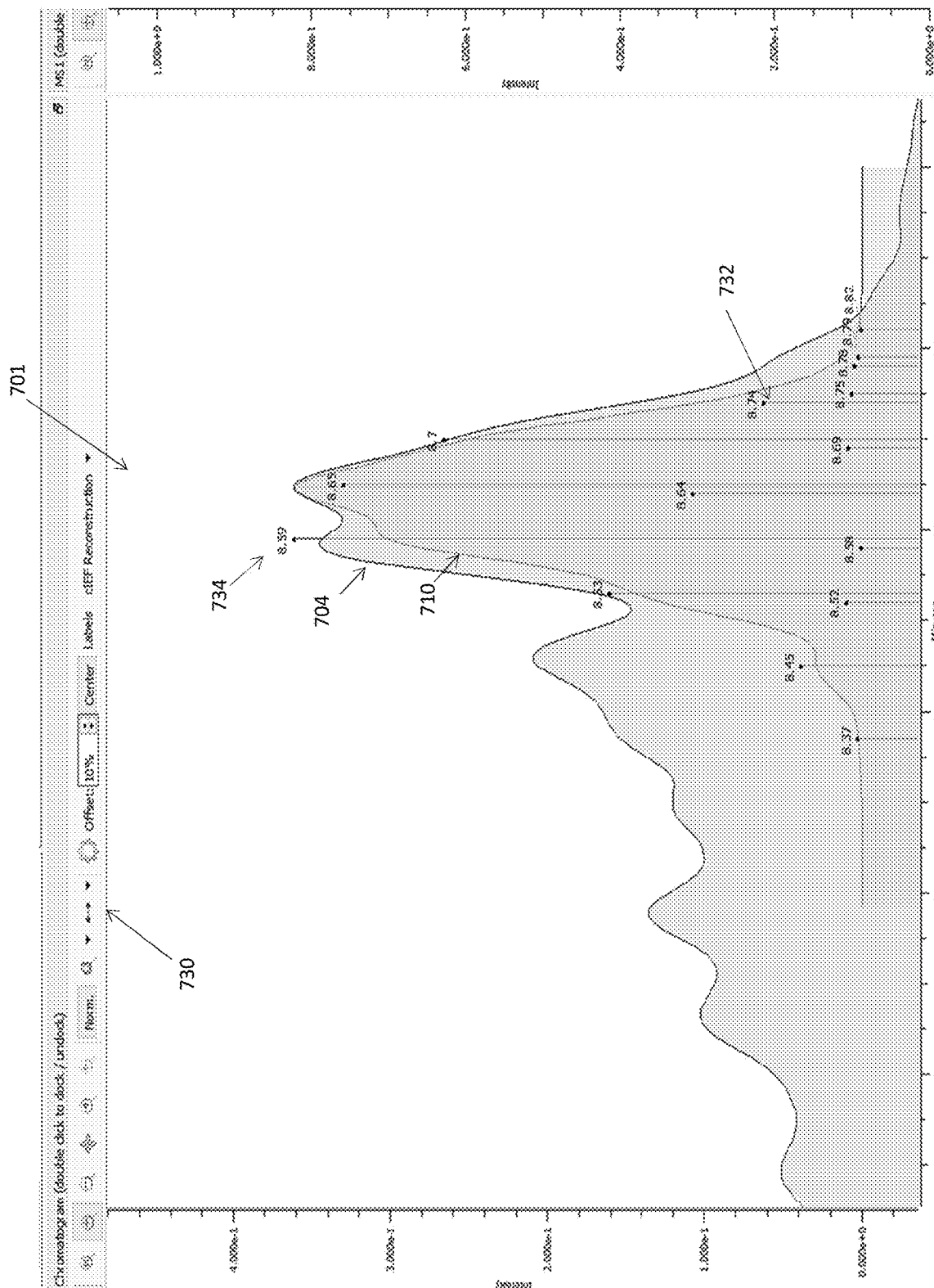
FIG. 7E illustrates another aspect of the GUI of FIGS. 7A(1) and 7A(2), showing how a user can display labels and data points in a theoretical electropherogram and an experimentally-derived electropherogram.

FIG. 7E shows an example close-up view of another peak in the chromatogram window 701. The chromatogram window 701 can include a number of viewing settings 730 that allow the user to choose how to display the experimentally-derived electropherogram 704 and/or the theoretical electropherogram 710. In example shown, the user has chosen to display the electropherograms with a particular offset (10%) and to include data points (e.g., 732) corresponding to molecular species found in the MS data. In some embodiments, the user can choose to display pI labels (e.g., 734) on or near the data points (e.g., 732), where the pI labels (e.g., 734) show the pI value associated with a corresponding molecular species.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for generating a pseudo-electropherogram of a protein or protein complex, the method comprising:
    receiving peptide-level mass spectrometry data including mass-to-charge ratio data associated with peptides of the protein or protein complex, wherein the mass-to-charge ratio data includes mass-to-charge ratio data associated with modified peptide forms;
    generating the pseudo-electropherogram based on all or a subset of the modified peptide forms, wherein generating the pseudo-electropherogram comprises:
        determining masses of the modified peptide forms based on the mass-to-charge ratio data associated with the modified peptide forms,
        matching reference peptide sequences of the protein or protein complex against the determined masses of the modified peptide forms to map the modified peptide forms to locations in the protein or protein complex, and
        combining calculated charge distributions of the modified peptide forms calculated based on isoelectric point to generate a distribution of charge variant forms of the protein or protein complex; and
    displaying the pseudo-electropherogram representing different charge variant forms of the protein or protein complex.

2. The method of claim 1, wherein the reference peptide sequences are in a reference list of peptide sequences.

3. The method of claim 1, wherein generating the pseudo-electropherogram includes estimating a relative abundance of each of the modified peptide forms based on mass spectrometric measurements of each corresponding modified peptide form.

4. The method of claim 1, wherein generating the pseudo-electropherogram includes charge normalizing one or more modification groups of the modified peptide forms.

5. The method of claim 1, wherein displaying the pseudo-electropherogram includes displaying an overlay of an experimentally-derived electropherogram with the pseudo-electropherogram.

6. The method of claim 5, wherein a peak associated with the protein in the experimentally-derived electropherogram is aligned with a peak associated with a corresponding protein in the pseudo-electropherogram.

7. The method of claim 5, wherein the experimentally-derived electropherogram includes capillary isoelectric focusing (ciEF) electropherogram data.

8. The method of claim 1, wherein the modified peptide forms include one or more modification groups, the one or more modification groups including one or more of a glycan group, a phosphate group, an amino group and a carboxyl group.

9. The method of claim 1, further comprising generating a pseudo-intact mass spectrum based on all or a subset of the modified peptide forms, and displaying the pseudo-intact mass spectrum to a user.

10. The method of claim 9, further comprising displaying the pseudo-electropherogram in a first window of a user interface and displaying the pseudo-intact mass spectrum in a second window of the user interface.

11. The method of claim 5, further comprising displaying one or more labels on or near a peak of the pseudo-electropherogram or the experimentally-derived electropherogram.

12. The method of claim 1, wherein the peptide-level mass spectrometry data is based on an enzyme-digested sample of the protein or protein complex.

13. A system, the system comprising:
    one or more processors; and
    a memory coupled to the one or more processors, the memory configured to store computer-program instructions, that, when executed by the one or more processors, perform a computer-implemented method comprising:
        receiving peptide-level mass spectrometry data including mass-to-charge ratio data associated with peptides of a protein or protein complex, wherein the mass-to-charge ratio data includes mass-to-charge ratio data associated with modified peptide forms;
        generating a pseudo-electropherogram based on all or a subset of the modified peptide forms, wherein generating the pseudo-electropherogram comprises:

determining masses of the modified peptide forms based on the mass-to-charge ratio data associated with the modified peptide forms, matching reference peptide sequences of the protein or protein complex against the determined masses of the modified peptide forms to map the modified peptide forms to locations in the protein or protein complex, and combining calculated charge distributions of the modified peptide forms calculated based on isoelectric point to generate a distribution of charge variant forms of the protein or protein complex; and displaying the pseudo-electropherogram to a user, wherein the pseudo-electropherogram represents different charge variant forms of the protein or protein complex.

14. The system of claim 13, wherein generating the pseudo-electropherogram includes charge normalizing one or more modification groups of the modified peptide forms, wherein generating the pseudo-electropherogram is based on different charge states of the modified peptide forms.

15. The system of claim 13, wherein the reference peptide sequences are in a reference list of peptide sequences.

16. The system of claim 13, wherein generating the pseudo-electropherogram includes predicting a relative abundance of each of the modified peptide forms based on a mass spectrometric measurement associated with each corresponding modified peptide form.

17. The system of claim 13, wherein displaying the pseudo-electropherogram includes displaying an overlay of an experimentally-derived electropherogram with the pseudo-electropherogram.

18. The system of claim 17, wherein a peak associated with a modified peptide form having in the experimentally-derived electropherogram is aligned with a peak associated with a corresponding modified peptide form in the pseudo-electropherogram.

19. The system of claim 13, wherein the modified peptide forms include one or more modification groups, the one or more modification groups including one or more of a glycan group, a phosphate group, an amino group and a carboxyl group.

20. The system of claim 13, wherein the computer-implemented method further comprises generating a pseudo-intact mass spectrum based on all or a subset of the modified peptide forms, and displaying the pseudo-intact mass spectrum to the user.

* * * * *